(12) United States Patent
Spillman et al.

(10) Patent No.: US 11,485,038 B2
(45) Date of Patent: Nov. 1, 2022

(54) METHOD FOR OPTIMIZED WOOD PRODUCTION IN A CHOP SAW

(71) Applicant: Eagle Machinery & Supply, Inc., Sugarcreek, OH (US)

(72) Inventors: Kirk Spillman, Zoar, OH (US); Todd Spillman, Mineral City, OH (US)

(73) Assignee: Eagle Machinery & Supply, Inc., Sugarcreek, OH (US)

( * ) Notice: Subject to any disclaimer, the term of this patent is extended or adjusted under 35 U.S.C. 154(b) by 0 days.

(21) Appl. No.: 16/831,036

(22) Filed: Mar. 26, 2020

(65) Prior Publication Data

US 2020/0307014 A1 Oct. 1, 2020

Related U.S. Application Data

(60) Provisional application No. 62/825,195, filed on Mar. 28, 2019.

(51) Int. Cl.
| | | |
|---|---|---|
| *B27B 5/22* | (2006.01) | |
| *B27B 5/29* | (2006.01) | |
| *B23D 59/00* | (2006.01) | |
| *B27B 5/18* | (2006.01) | |
| *B27G 19/02* | (2006.01) | |

(52) U.S. Cl.
CPC ............ *B27B 5/228* (2013.01); *B23D 59/001* (2013.01); *B23D 59/008* (2013.01); *B27B 5/18* (2013.01); *B27B 5/29* (2013.01); *B27G 19/02* (2013.01)

(58) Field of Classification Search
CPC .. B27B 5/228; B27B 5/18; B27B 5/29; B23D 59/001; B23D 59/008; B27G 19/02

USPC .................................................... 83/365, 371
See application file for complete search history.

(56) References Cited

U.S. PATENT DOCUMENTS

| | | | | |
|---|---|---|---|---|
| 3,608,594 | A * | 9/1971 | Holderried | B27B 5/18 83/318 |
| 3,760,667 | A * | 9/1973 | Maxey | B27L 5/08 83/365 |
| 4,221,974 | A * | 9/1980 | Mueller | B23D 59/008 250/559.48 |
| 4,397,204 | A * | 8/1983 | Colombo | B26D 1/626 83/365 |
| 5,099,896 | A * | 3/1992 | Ritola | B27B 5/228 144/2.1 |
| 5,826,481 | A * | 10/1998 | Sintonen | B27L 5/08 83/664 |
| 6,923,101 | B2 * | 8/2005 | Culpepper | B23D 45/20 83/287 |
| 9,957,114 | B2 | 5/2018 | Beesley | |
| 2003/0154834 | A1 | 8/2003 | Cothrell | |
| 2010/0012227 | A1 * | 1/2010 | Zielke | B23K 26/032 144/392 |

\* cited by examiner

*Primary Examiner* — Omar Flores Sanchez
(74) *Attorney, Agent, or Firm* — Sand, Sebolt & Wernow Co., LPA

(57) ABSTRACT

An automated crosscut saw system utilizing a wood scanning unit to optimize the cuts in a particular piece of wood to remove defects or flaws and a method of use therefor is provided. The automated saw system has the ability to scan and cut a piece of wood simultaneously or in rapid succession without the need for scanning the entire length of the wood prior to cutting. Further, the automated saw system may eliminate the need for a secondary feeder and secondary queue.

24 Claims, 22 Drawing Sheets

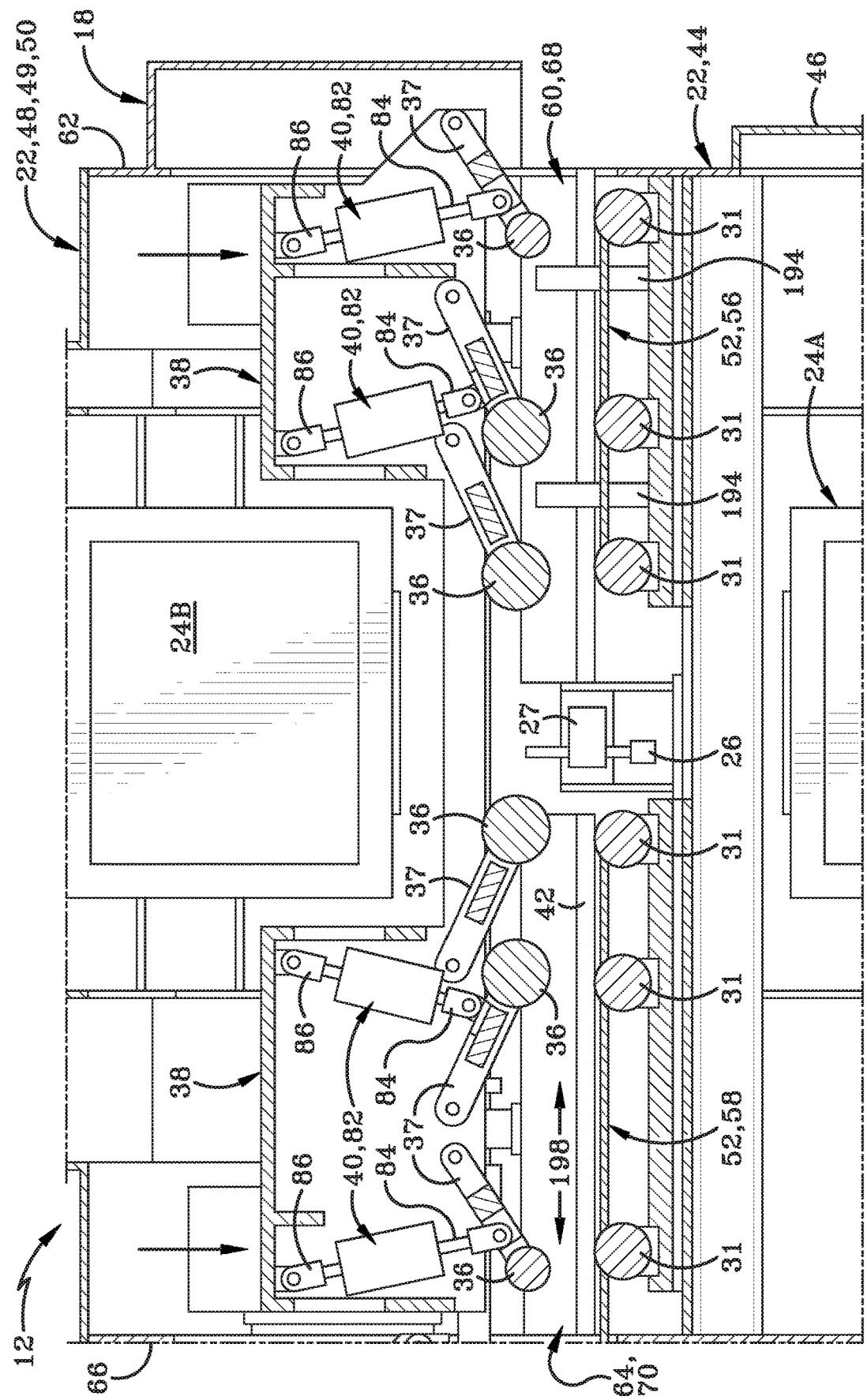

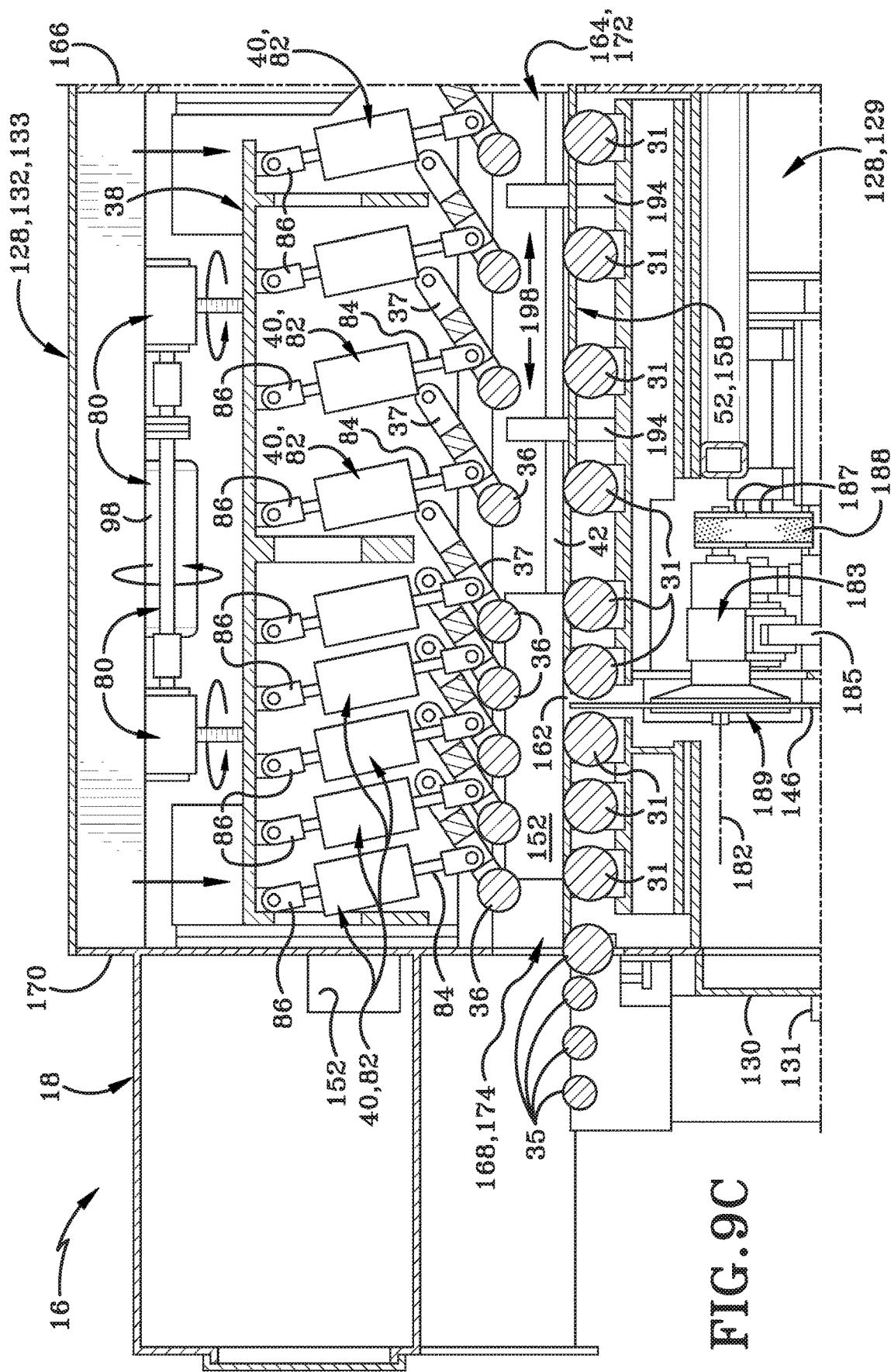

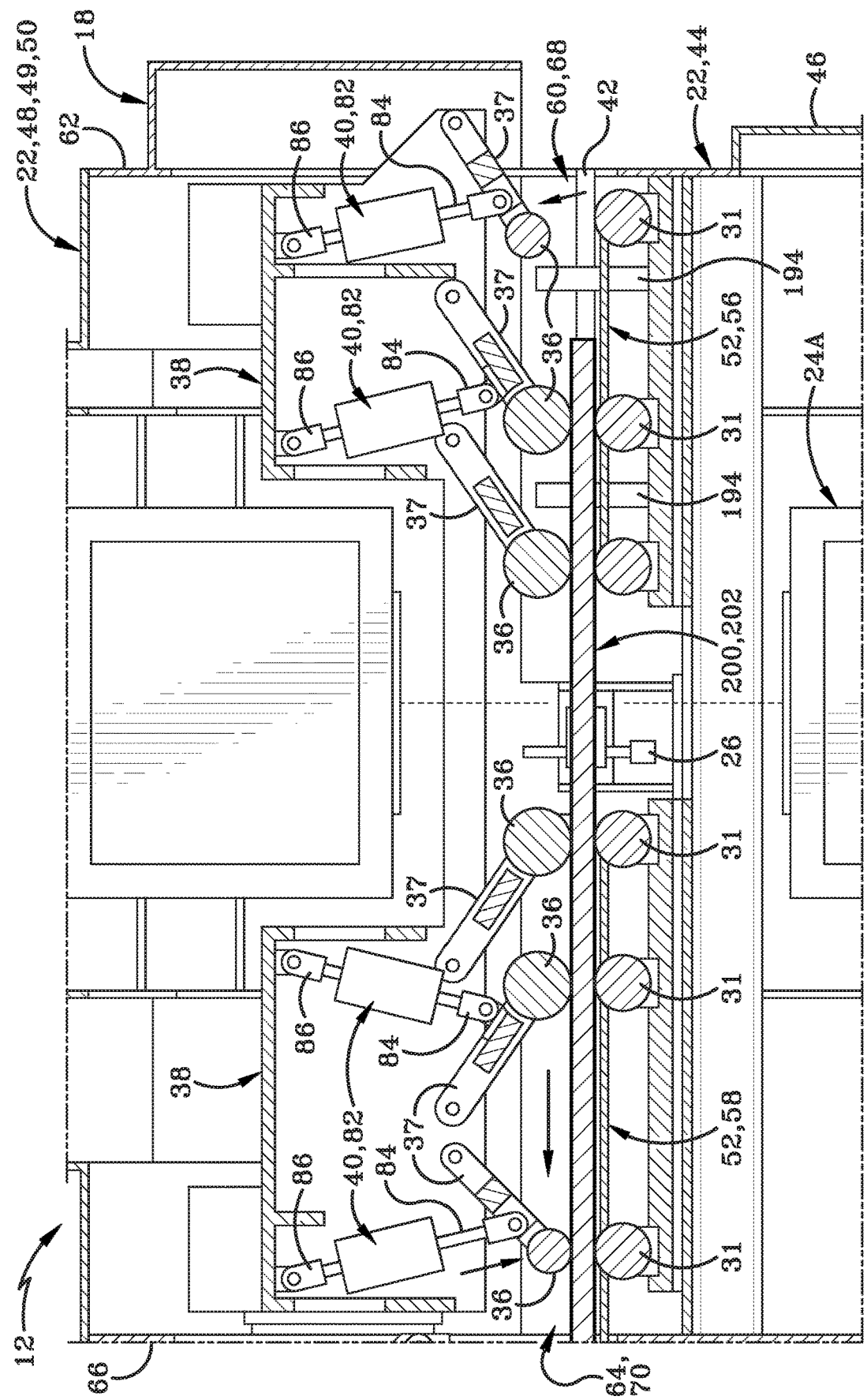

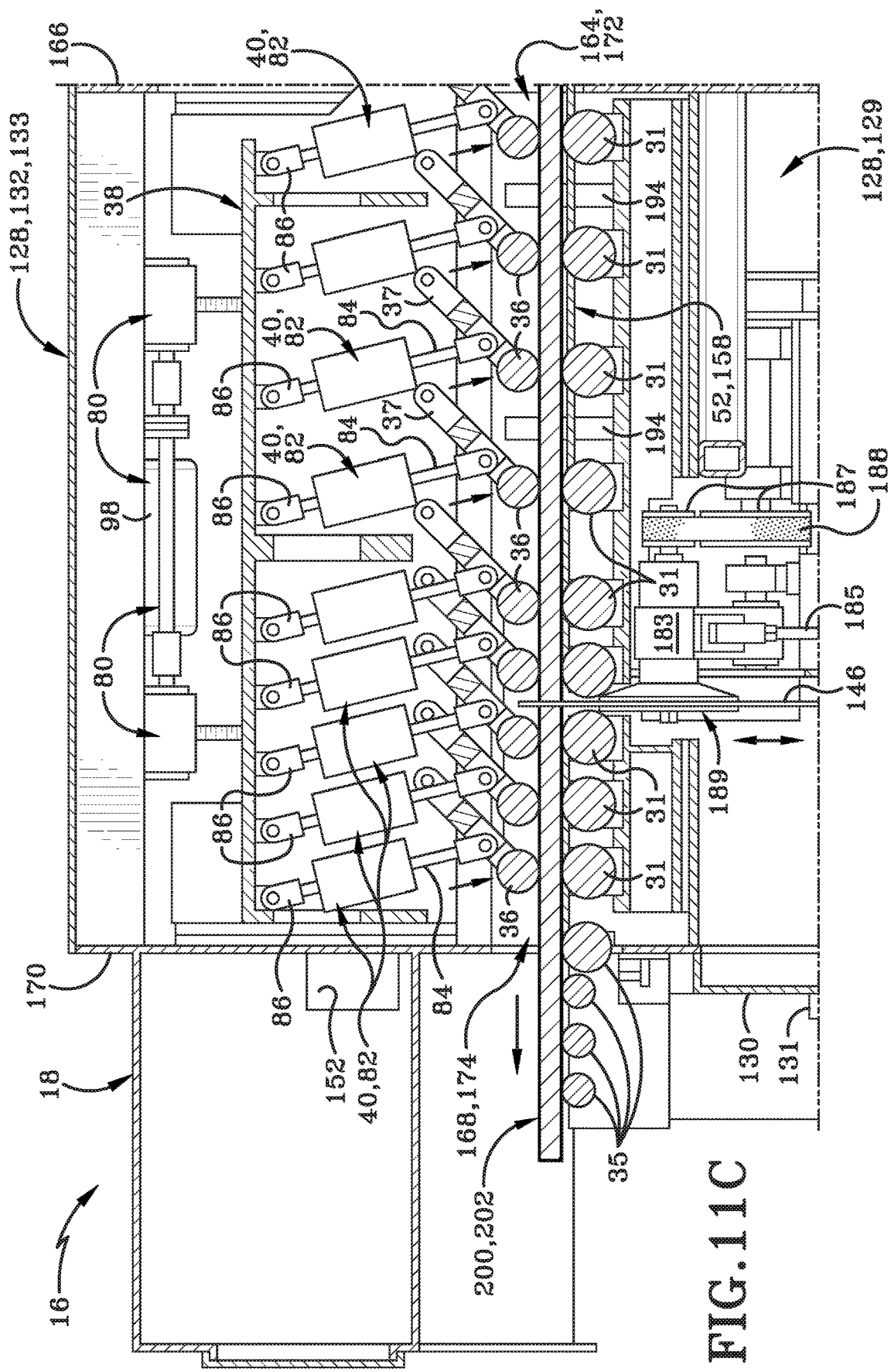

METHOD FOR OPTIMIZED WOOD PRODUCTION IN A CHOP SAW

CROSS REFERENCE TO RELATED APPLICATIONS

This application claims the benefit of U.S. Provisional Application Ser. No. 62/825,195, filed on Mar. 28, 2019; the disclosure of which is incorporated herein by reference.

BACKGROUND

Technical Field

The present disclosure relates generally to the field of automated crosscut saws. More particularly, the present disclosure relates to an automated crosscut saw with a wood scanning system for wood usage. Specifically, the present disclosure relates to an automated crosscut saw utilizing a wood scanning system to optimize the cuts in a particular piece of wood to remove defects or flaws and a method of use therefor. The automated saw system further has the ability to scan and cut a piece of wood simultaneously or in rapid succession.

Background Information

Current automated crosscut saw systems generally utilize a wood scanner or wood optical scanner to detect flaws in a piece of lumber and an automatically controlled crosscut saw, or chop saw, to remove defects identified by the scanner from a specific piece of lumber. Current systems are large and unwieldy and take significant floor space in a wood processing facility as they typically utilize multiple wood queues wherein boards are queued prior to being put through the optical scanner and again after being scanned, but prior to being fed through the chop saw. Typically, these queues are managed and moved by automated feeder systems which can allow the boards to be loaded and then automatically fed through the scanner and to the next feeder. The second feeder may then manage the second queue and may proceed to pass the boards to the chop saw for cutting. Current systems utilize scanners and scanning method that require the entire board to be scanned before the board can be cut to remove defects and flaws therein. These scans are saved in a scan file or scan profile that is then communicated to the saw which must then keep accurate order of the scan files to ensure that the identified defects are removed from the correct board. Accordingly, the chop saw is typically operating multiple boards ahead of the scanner to allow sufficient time for the scanner to complete a total scan of each board.

In current systems, as wood travels through the scanner and enters the pre-saw queue it is common that a board may become displaced, dislodged, or may be disoriented in some way that is inconsistent with the scan file queue (such as flipped or turned, or the board may be in the pre-saw queue in the incorrect order), which may result in incorrect cuts being made, either by cutting the incorrect board or cutting a board in the incorrect place. Therefore, when a board is flipped, rotated, or otherwise disrupted in the queue, common practice is to halt the operation of the scanner and saw and clear the secondary queue, deleting all of the scan files and "flushing" the system. Each board is then removed from the secondary queue and must be placed back into the scanning queue to be rescanned prior to cutting. The process of clearing the queue and moving boards back into the scanning queue is time lost as the automated saw system is offline until the queue is cleared and the boards are replaced. Further, the boards have to be scanned a second time, again eating into valuable production time.

Wood is commonly moved through these current systems via the use of chains, paddles, continuous conveyor belts, or continuous belt-driven rollers. Specifically, the feeders typically use chains and/or conveyors to move the wood across the feeder to a belt or roller set that will move each individual board into the scanner or saw. The feeders must accommodate multiple boards that may vary in length, thus the feeders tend to be very large and take up significant space within current systems. Further, current scanners typically must scan the entire length of each section of board prior to cutting the defects therefrom and/or optimizing the board usage to meet a predetermined cut list. Thus, current systems require sufficient space between the scanner and the saw to allow even longer boards to pass through the scanner prior to cutting. Finally, although the feeders are large, and significant space is utilized between the scanners and the saws to accommodate longer boards, the size of the feeders used provide a length limitation on the boards that may be processed by current systems. For example, if the feeder is fourteen feet wide, the maximum board length that may be processed might be fourteen feet, and boards exceeding the maximum length must be cut prior to feeding them into a current system. This may increase the number of times each board must be handled, and may further require additional equipment to cut the boards. Alternatively, having a length limitation may dictate what products may be produced by an automated saw system, and may limit that system from flexibility in producing multiple types of goods.

SUMMARY

The present disclosure addresses these and other issues by providing an automated crosscut saw including a wood scanning system and chop saw that operate and communicate in real time to allow a board to be simultaneously scanned and cut and/or for a board being scanned to be the next board to encounter the saw to be cut. The present automated saw system may further allow for elimination of the secondary queue, thus saving significant space and cost, as well as reducing or eliminating the need to clear the queue and re-scan boards due to misalignment, misplacement, or disorientation of the boards in the secondary queue. Finally, the present saw system may allow for processing boards of indiscriminate length without the need for additional space or equipment.

According to one aspect, one exemplary embodiment of the present disclosure may provide a method of cutting a piece of wood comprising: inserting a first end of a piece of wood into a scanning unit of an automated saw system; scanning a first portion of the piece of wood for one or more defects via at least one optical scanner; directing the piece of wood along a path through the saw system directly into a cutting unit; and cutting the first portion of the piece of wood while simultaneously scanning a second portion of the piece of wood with the at least one optical scanner.

According to another aspect, one exemplary embodiment of the present disclosure may provide a method of optimized wood production comprising: inserting a first piece of wood into a scanning unit of an automated saw system; scanning a first portion of the first piece of wood for one or more defects via at least one optical scanner; directing the first portion of the first piece of wood along a path through the saw system directly into a cutting unit; cutting the first portion of the first piece of wood with the cutting unit while simultaneously scanning a second portion of the first piece of wood with the at least one optical scanner; directing the second portion of the first piece of wood to the cutting unit while simultaneously inserting a second piece of wood into the scanning unit; and cutting the second portion of the first piece of wood with the cutting unit while simultaneously scanning a first portion of the second piece of wood with the at least one optical scanner.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 9A is a close up front elevation cross sectional view of the scanning unit of an automated saw system from FIG. 5A, according to one aspect of the present disclosure.

FIG. 9C is a close up front elevation cross sectional view of the cutting unit of an automated saw system from FIG. 5C, according to one aspect of the present disclosure.

FIG. 11A is an operational front elevation cross sectional view showing a first board to be cut moving through the scanning unit of an automated saw system from FIG. 9A, according to one aspect of the present disclosure.

FIG. 11C is an operational front elevation cross sectional view showing a board to be cut moving through the cutting unit of an automated saw system from FIG. 9C, according to one aspect of the present disclosure.

Similar numbers refer to similar parts throughout the drawings.

DETAILED DESCRIPTION

Figure 1:
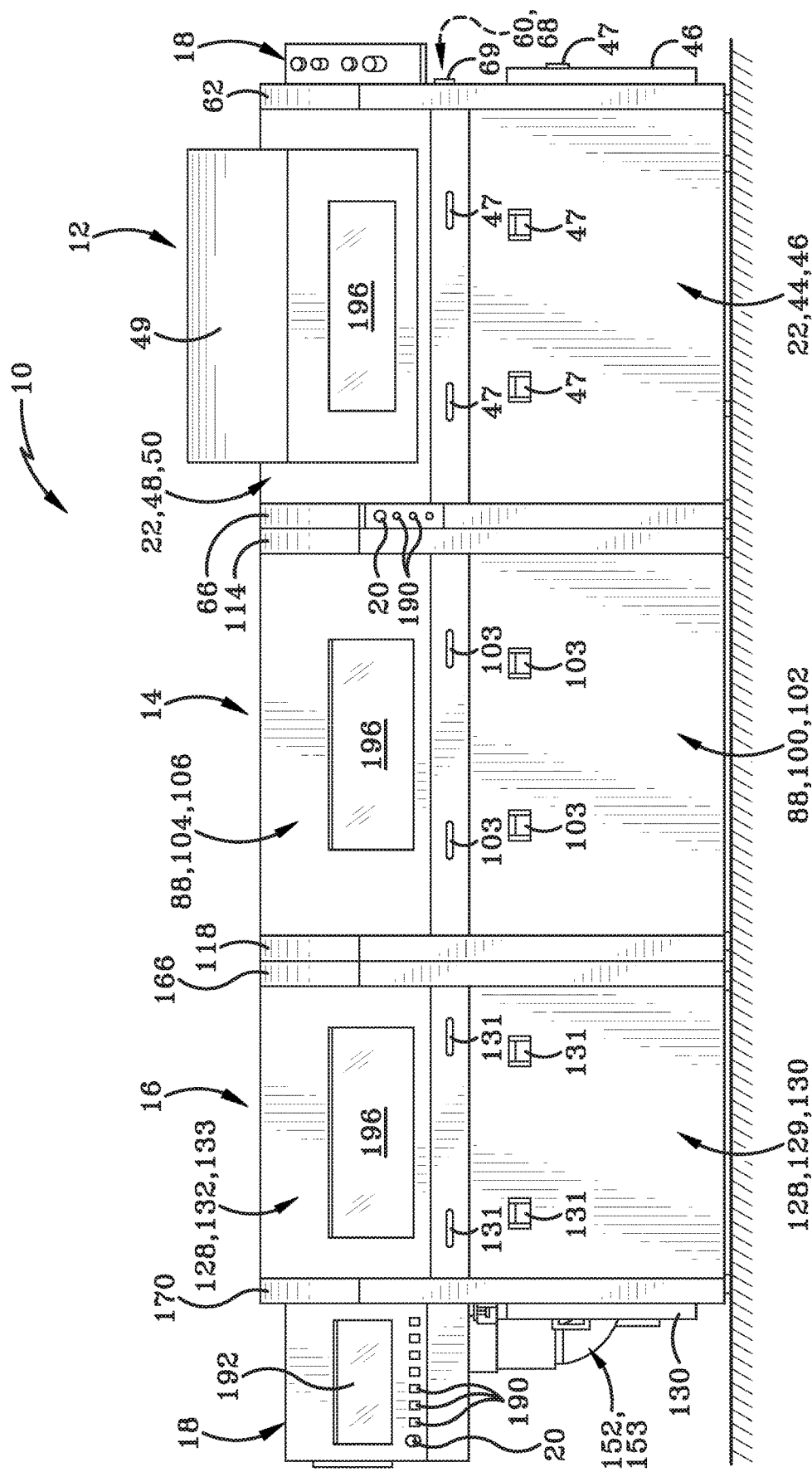
FIG. 1 is a front elevation view of an automated saw system according to one aspect of the present disclosure.
Figure 2:
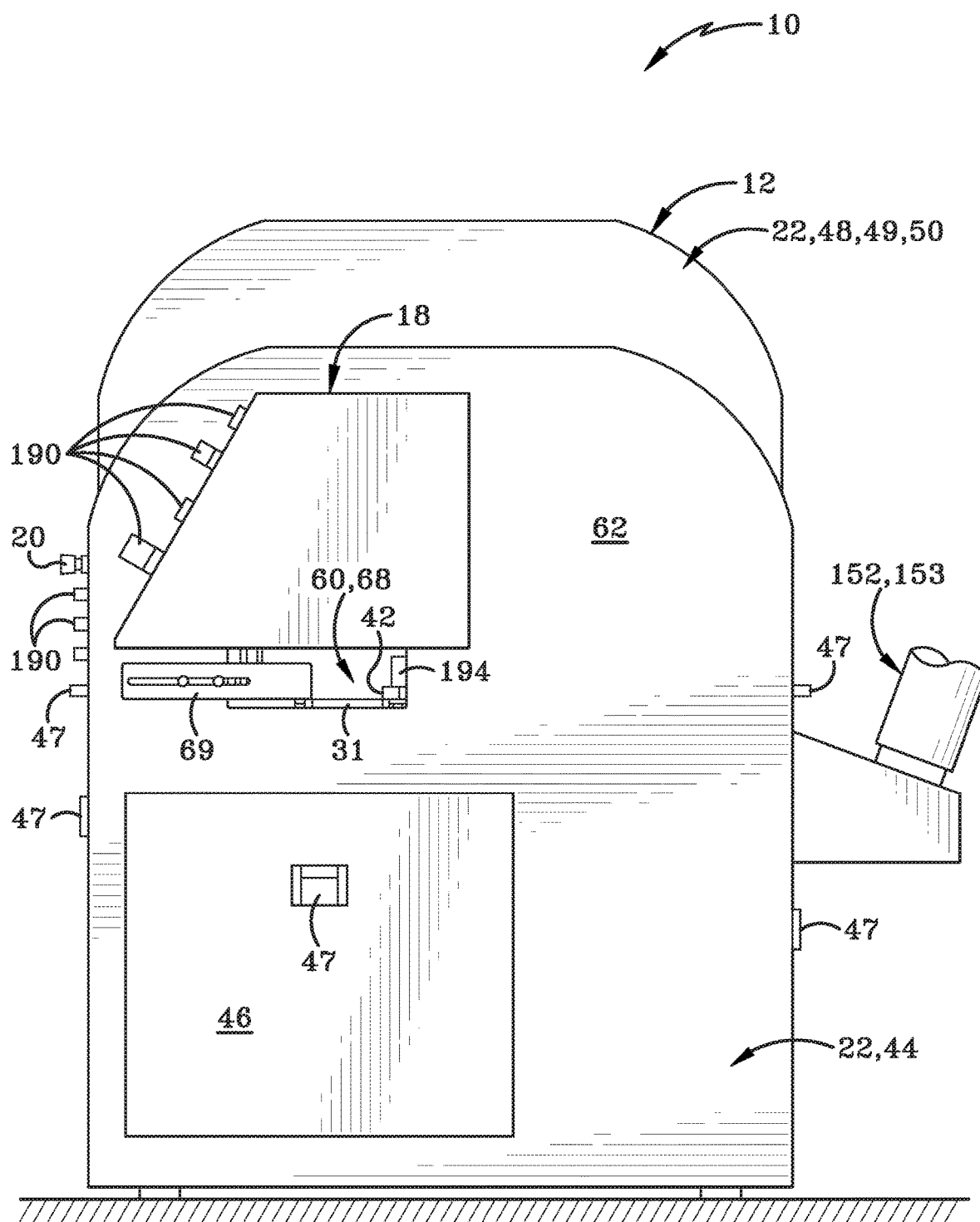
FIG. 2 is a right side elevation view of an automated saw system according to one aspect of the present disclosure.
Figure 3:
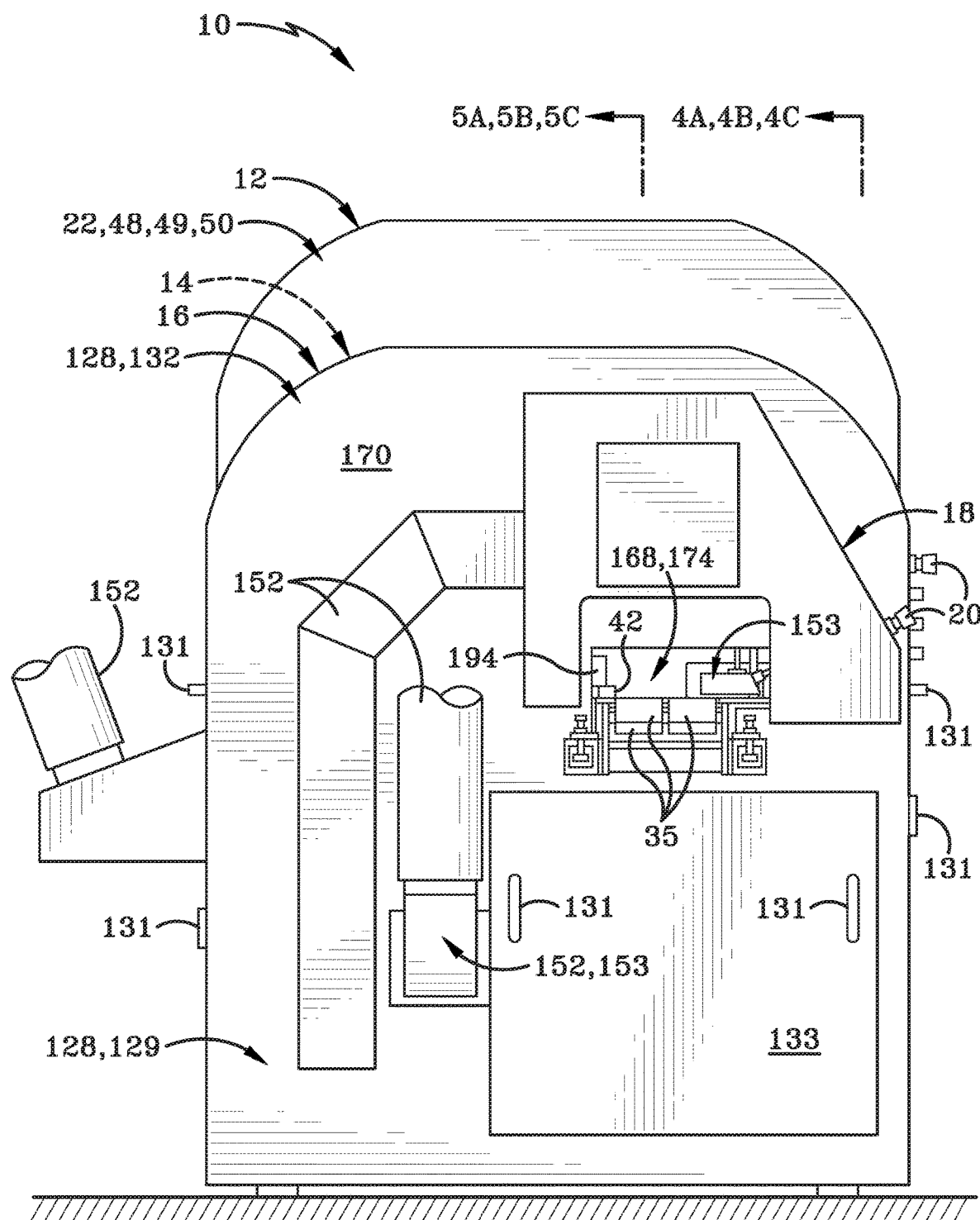
FIG. 3 is a left side elevation view of an automated saw system according to one aspect of the present disclosure.
Figure 4A:
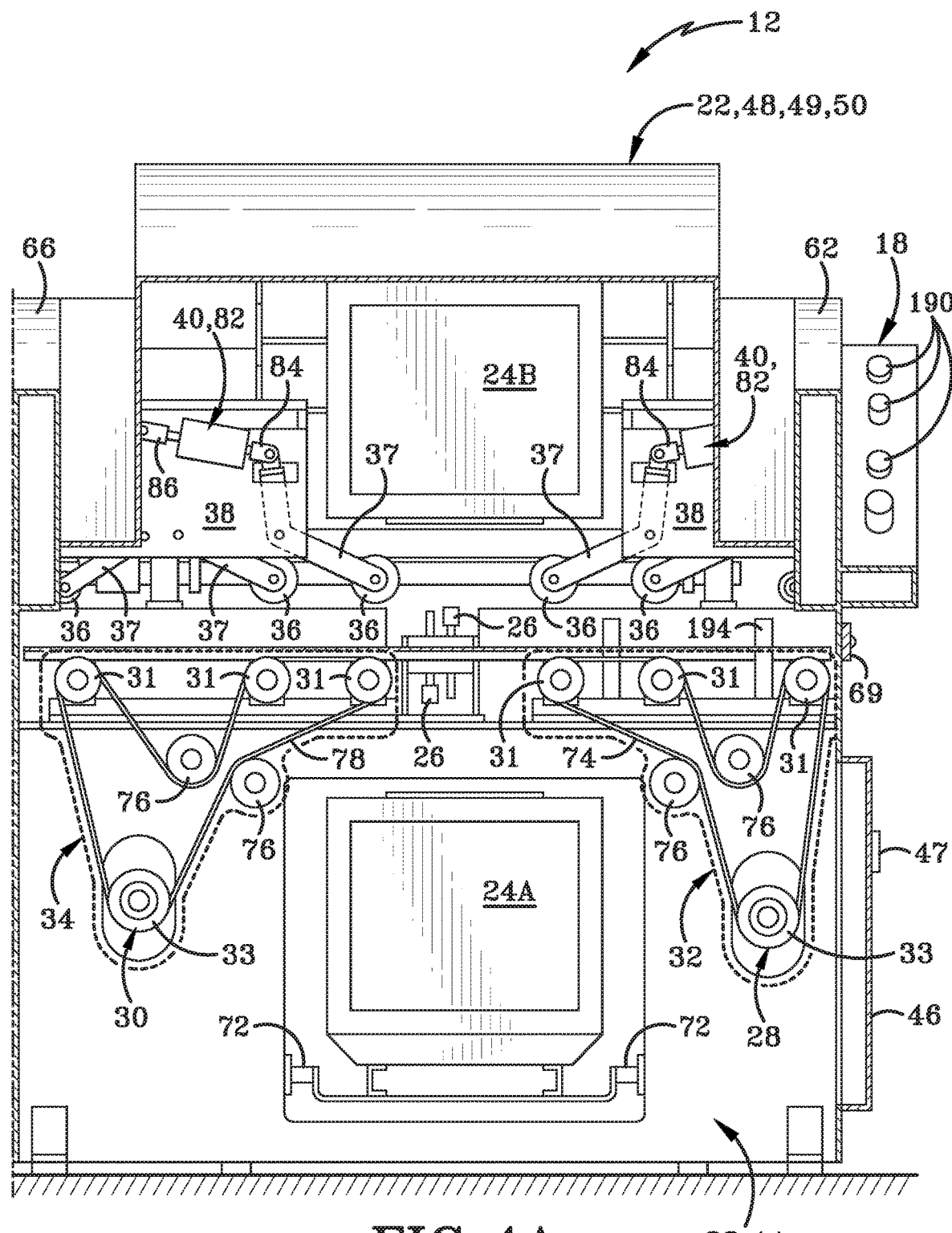
FIG. 4A is a first front elevation cross sectional view of a scanning unit of an automated saw system taken along line 4-4 indicated in FIG. 3, according to one aspect of the present disclosure.
Figure 4B:
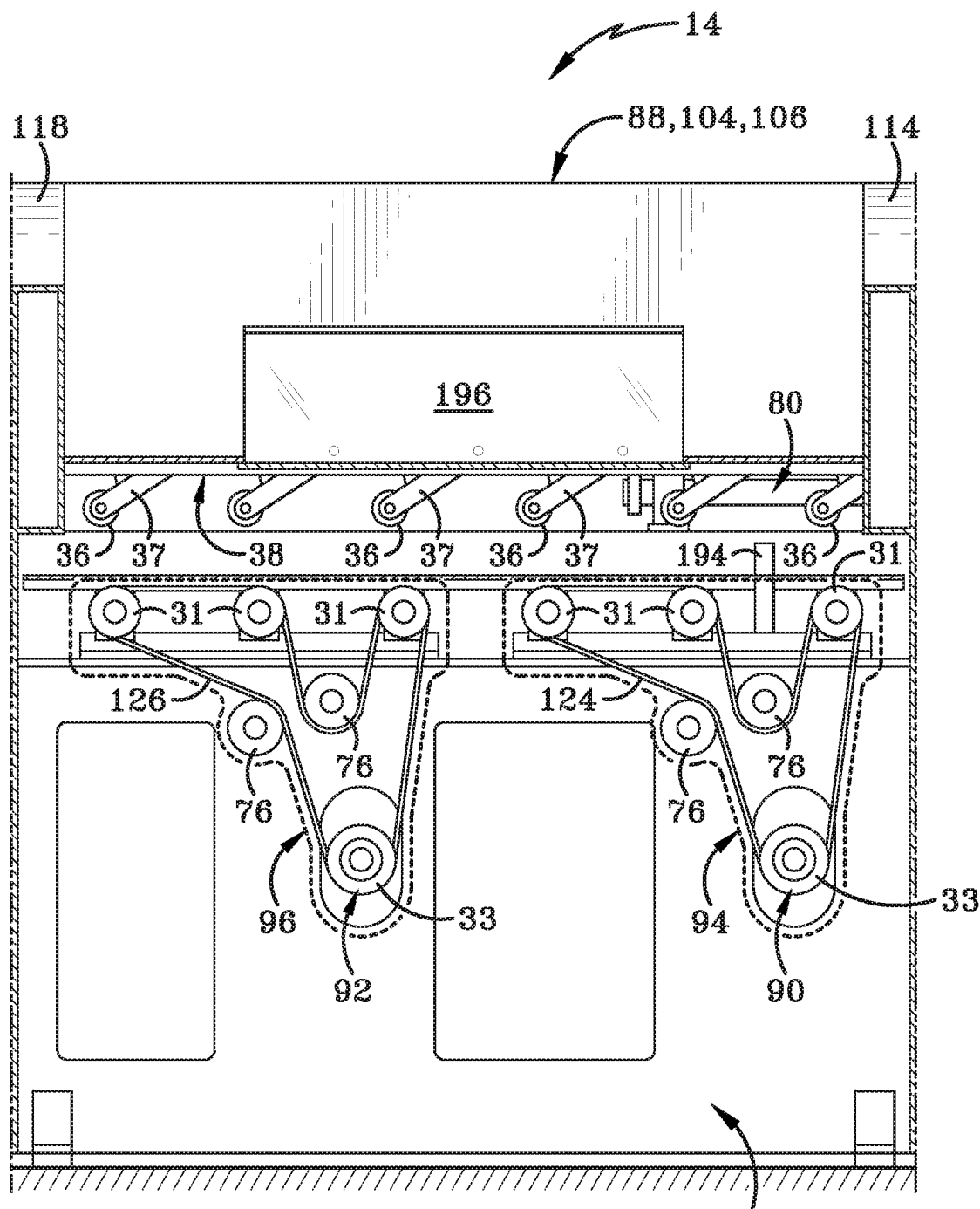
FIG. 4B is a first front elevation cross sectional view of a transition unit of an automated saw system taken along line 4-4 indicated in FIG. 3, according to one aspect of the present disclosure.
Figure 4C:
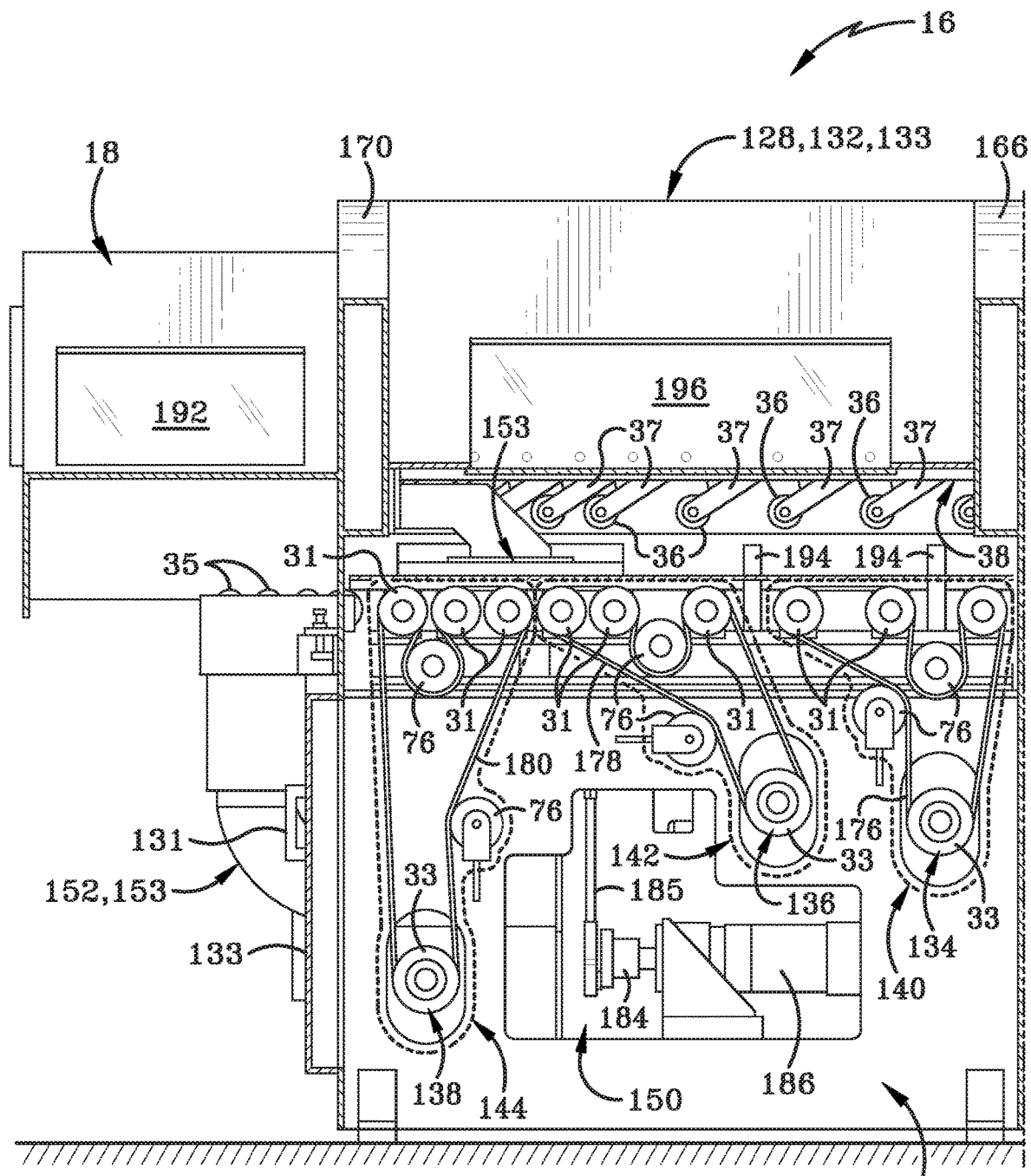
FIG. 4C is a first front elevation cross sectional view of a cutting unit of an automated saw system taken along line 4-4 indicated in FIG. 3, according to one aspect of the present disclosure.

With reference to FIGS. 1-9C, an automated crosscut saw system 10 of the present disclosure is shown having an optical scanning unit 12, a transition unit 14, a cutting unit 16, and one or more control panels 18, which may be arranged in a linear unit. As shown in the figures and discussed throughout, the saw system 10 may have the scanning unit 12 separated from the cutting unit 16 by the transition unit 14, however, it will be understood that the order in which they are presented and discussed may be reversed. For example, with reference to FIG. 1, the scanning unit 12 is depicted to the right of the transition unit 14, but in practice the scanning unit 12 may be on either the right or the left of the transition unit 14. Similarly, the cutting unit 16 may be on either the right or the left, opposite the scanning unit 12. The path 198 through saw system 10 taken by a piece of wood 200 may likewise be reversed depending upon the specific implementation.

Automated crosscut saw system 10, or saw system 10, may be electrically controlled and may include appropriate electrical connections, including one or more power connections. Saw system 10 may also include suitable connections to various external components, such as pneumatic connections, hydraulic connections, or any other required connections as dictated by the desired implementation. It will be understood that these connections may be made using industry standard materials suitable for the desired purpose. It will be further understood that these systems and/or connections may or may not be present in all units of the saw system 10, or alternatively may or may not be present in the saw system 10 at all depending on the desired implementation. Therefore, these connections, and the particulars of the associated systems therewith, are omitted from further discussion herein for purposes of clarity and brevity in the disclosure.

Saw system 10, and the various components thereof, as discussed herein, may include additional elements, such as braces, flanges, mounting points, mounting brackets, structural members, linkages, pulleys, belts, electronic components, optical components, pneumatic components, hydraulic components, data connections, communications components, wiring, hoses, hardware, or the like that may be utilized to connect, mount, support, and/or control saw system 10 and its components thereof. These additional elements and components may vary depending on the specific implementation parameters of saw system 10, and may be included or excluded as necessary to allow for the configuration and operation of saw system 10. It will be understood that these components and element are presumed present within saw system 10, unless specifically stated to the contrary, but are otherwise hereinafter excluded from discussion for purposes of brevity and clarity in the disclosure.

Saw system 10 may include a safety shut-off system that may include one or more emergency shut-off switches 20 and/or automatic shut-off systems. This safety system may be placed anywhere on or within the saw system 10, provided it does not interfere with other components thereof. Any such safety system may comport with industry standards and/or safety regulations and may be any suitable safety system as dictated by the desired implementation. Accordingly, any safety system or systems present in saw system 10 will be understood to operate according to its expected function, and may include any and all necessary parts to accomplish such operation, unless specifically stated otherwise.

The optical scanning unit 12, or scanning unit 12, may have a housing 22 which may enclose one or more optical scanners, shown in the figures as lower scanner 24A and upper scanner 24B, operable to visualize both the bottom and top of a piece of wood 200. Scanning unit 12 may further include one or more scanning lasers 26, a first servo motor 28, a second servo motor 30, a plurality of rollers 31 arranged into a first roller set 32 operationally connected to the first servo motor 28 and a second roller set 34 operationally connected to the second servo motor 30, a plurality of guide rollers 36 contained or otherwise connected to a guide roller housing 38, and a plurality of pneumatic actuators 40. Optical scanning unit 12 may further include a computer, processor or the like which may control the optical scanners 24 as well as the first and second servo motors 28, 30, and may be in communication with one or more computers or processors in the transition unit 14 and/or cutting unit 16, as discussed further herein. Various other components within optical scanning unit 12 may be discussed further below with relation to the operation thereof.

The housing 22 of scanning unit 12 may have a lower or bottom portion 44 which may contain the lower optical scanner 24A, the first and second servo motors 28, 30, and the first and second roller sets 32, 34 therein. Bottom portion 44 of the housing 22 may have one or more removable panels 46 with one or more handles 47 thereon to allow an operator access to the components contained therein for maintenance and the like. The housing 22 of scanning unit 12 may also have an upper or top portion 48 with one or more access doors 50 to allow an operator access to the interior of the scanning unit 12, including the top of the first and second roller sets 32, 34 and the path 198 a piece of wood 200 may take as it travels through the scanning unit 12. The access door 50 may have an increased clearance by way of an extended central portion, or hood 49, which may allow additional interior space to accommodate the upper optical scanner 24B, as well as the guide rollers 36, guide roller housing 38, and pneumatic actuators 40, as discussed further below. Hood 49 may be integrally formed with access door 50 and, according to one aspect, may be considered a single structure therewith. According to another aspect, hood 49 may be separate from access door 50, or may alternatively be fixed with access door 50 defined therein. Access door 50 and/or hood 49 may include one or more transparent panes, illustrated as window 196, which may facilitate an operators' ability to view wood 200 moving through scanning unit 12 to monitor for proper operation, component positioning, maintenance concerns, or the like while safely containing the components of scanning unit 12 and wood 200 therein. According to one aspect, window 196 may be constructed of any suitable transparent or partially transparent material, including glass, safety glass, plastic, acrylic, or the like. According to another aspect, window 196 may be omitted, as desired or necessary.

The separation between lower and upper portions 44, 48 of the housing 22 of the scanning unit 12 may be defined by one or more plates 52, which may be arranged into a first plate 56 and a second plate 58. Plates 52 may further have a plurality of openings 54 defined therein that may each correspond to a roller 31, with the first plate 56 having openings 54 defined therein for the rollers 31 of the first roller set 32 and the second plate 58 having openings 54 defined therein for the rollers 31 of the second roller set 34. The first and second plates 56, 58 may be spaced apart longitudinally to allow the lower optical scanner 24A to scan the bottom of a piece of wood 200, as discussed further herein. Plates 52 may be formed of any suitable material including metal, plastic, high-density polyethylene or other polymers, or the like. Plates 52 may be polished or coated to reduce friction between plates 52 and a piece of wood 200 moving through saw system 10.

The housing 22 of the scanning unit 12 may have a first pass-through opening 60 defined in a first side 62 thereof and a second pass-through opening 64 defined in a second side 66 thereof. The first side 62 may be determined as the side of the scanning unit 12 that may accept a new piece of wood 200 from an operator or from a feeder while the second side 66 may be opposite thereto, as discussed below. Therefore, the first opening 60 may further define the entrance 68 into the scanning unit 12 for a piece of wood 200 to be scanned while the second opening 64 may then define the exit 70 from the scanning unit 12. The entrance 68 to the scanning unit may include a horizontal adjustment slider 69 that may be adjusted to narrow or widen the entrance 68 to accommodate pieces of wood 200 with varying widths, holding one side of the wood 200 against the slider 69 and another side against a fence 42 that may run substantially the entire length of the wood path 198 through saw system 10, as discussed below.

The housing of scanning unit 12 may further include mounting points for emergency start/stop switches 20, power switches, or the like. Further, as discussed below, housing of scanning unit 12 may include a mounting point or bracket for mounting one of the one or more control panels 18 thereto, if desired.

The one or more optical scanners 24 may include the upper optical scanner 24B and the lower optical scanners 24A, which may be high frame rate cameras or any other suitable camera as dictated by the desired implementation. According to one aspect, optical cameras may be WoodEye cameras available commercially from WoodEye AB (Sweden). According to one aspect, saw system 10 may include additional optical scanners 24. According to another aspect, saw system may include a single optical scanner 24 as dictated by the desired implementation.

The one or more scanning lasers 26 may be mounted to the scanning unit 12 via laser mounts 27 and may include one or more lasers 26 that project onto the top, bottom, and/or side surfaces of the wood 200 as it moves through the scanning unit 12. These lasers 26 may be any suitable laser 26 types, and may be or further include a laser 26 generator and/or receiver optic that are operable to produce a suitable laser 26 and to detect surface variations on the wood 200 as it moves through the scanning unit 12. Scanning lasers 26 may be adjustable in position and angle, and/or in laser wavelength or type as dictated by the desired implementation. Adjustments to the laser(s) 26 may be manual or automatic, and the lasers 26 and/or laser mounts 27 may include motorized components that may allow for motorized adjustments thereto, as desired.

First and second servo motors 28, 30 may be any suitable servo type motor that is operable to drive first and second roller sets 32, 34. According to one aspect, first and second servo motors 28, 30 may be any suitable motor or actuator allowing for precise control of the rollers 31, as discussed herein. First and second servo motors 28, 30 may further include one or more sensors, control modules, or the like, as necessary for operation and control thereof. According to another aspect, first and second servo motors 28, 30 may be any suitable for use in a closed loop system or suitable for precise control of rollers 31, as discussed herein. First and second servo motors 28, 30 may each include a drive roller 33 which may interact with related drive belts (discussed more fully below) to allow first and second servo motors 28, 30 to interact with rollers 31 of saw system 10.

Rollers 31 may be formed of any suitable material, including steel or other metals, polymers, plastics, or the like and may include a surface texture to aid in gripping or otherwise moving wood 200 along path 198 through saw system 10. Rollers 31 may be mounted in a sufficient manner as to permit them to rotate about a longitudinal axis running through each roller 31. Rollers 31 may further include a projection, extension, flange, groove, channel, or the like to permit interaction between rollers 31 and drive belts associated with each roller set and/or servo motor, as discussed herein. Rollers 31 may be of any suitable size, and saw system 10 may include multiple rollers of varying sizes depending upon their placement and/or function within saw system 10. According to one aspect, rollers 31 in one unit (e.g. scanning unit 12) may be substantially the same size and/or material while rollers in another unit (e.g. transition unit 14), may be substantially the same size and/or material but may differ from those rollers 31 in the other units.

According to another aspect, rollers 31 may vary within units or even within the same roller set, as desired and/or dictated by the desired implementation. Saw system 10 may further include additional rollers that are not part of any one roller set, such as exit rollers 35, discussed below. These additional rollers may be supplemental to rollers 31 in that they may be freely spinning and may be included within, or excluded from, saw system 10 as needed or desired to help facilitate the movement of wood 200 through the system 10.

As rollers 31 within scanning unit 12 (and within saw system 10 generally) may be arranged in sets, e.g. first roller set 32 and second roller set 34, first servo motor 28 may be connected to the first roller set 32 via a first drive belt 74, and may further utilize one or more tensioning rollers 76 to maintain the appropriate tension on the first drive belt 74. The first roller set 32 may include one or more individual rollers 31 and may be defined by its position within saw system 10. Specifically, first roller set 32 may be the roller set closest to the entrance 68 of scanning unit 12 (i.e., the first set encountered by a piece of wood 200 as it enters the saw system 10), as discussed below. Similarly, the second servo motor 30 may be connected to the second roller set 34 via a second drive belt 78, including with one or more tensioning rollers 76. Second roller set 34 may likewise be defined by its position within saw system 10 as the next set of rollers 31 encountered by the piece of wood 200 after the first roller set 32, as the wood 200 moves along wood path 198 and through the saw system 10, as further discussed herein. According to one aspect, first and/or second roller sets 32, 34 may include at least one roller 31 and at least one tensioning roller 76, along with the associated servo motor and drive roller 33 that are all connected or controlled by a single drive belt. For example, first roller set 32 is contemplated to include one or more rollers 31, tensioning roller(s) 76, first servo motor 28, drive roller 33, and first drive belt 74 to complete a "closed system" meaning that first roller set 32 can operate independently from other roller sets, such as second roller set 34.

Scanning unit 12 may further include a plurality of guide rollers 36 extending at downward from a mounting unit or housing 38 towards the wood path 198 and/or rollers 31. As contemplated and illustrated herein, guide rollers 36 are understood to be the rollers that are above the wood path 198 while rollers 31 are understood to be the rollers below the wood path 198 such that when a piece of wood 200 is present within saw system 10, the guide rollers 36 will interact with a top surface thereof while the rollers 31 will interact with a bottom surface thereof. According to one aspect, guide rollers 36 may be numbered and positioned to have a guide roller 36 positioned vertically above each roller 31 such that when the rollers 31 and guide rollers 36 engage a piece of wood 200, the rollers 31 and guide rollers 36 are directly opposite one another on the wood 200. According to another aspect, guide rollers 36 may be spaced and positioned as needed, desired, and/or dictated by the specific implementation thereof. Guide rollers 36 may be constructed of any suitable material, including metal, plastic, polymers, or the like, and may be uniformly sized, or may vary in size and/or material according to their placement and/or role within saw system 10.

Guide rollers 36 may be mounted or otherwise be connected to guide roller housing 38 via one or more arms 37. Arms 37 may be angled to place guide rollers in the proper position and orientation relative to the piece of wood 200 as to minimize damage, obstruction, and/or undesired resistance to the wood 200 as it moves along path 198 through system 10. Arms 37 may include a connector, mount, bracket, or the like that may support guide rollers 36 thereon while allowing the free rotation thereof.

Guide roller housing 38 may include a coarse adjustment system 80 operable to raise or lower a plurality of guide rollers 36 in unison. Coarse adjustment system 80 may include an adjustment motor 98 which may be connected to the guide roller housing 38 directly or alternatively though a series of secondary components. For example, adjustment motor 98 may connect to adjustment system 80 via one or more belts, chains, linkages, rods, axles, or the like, and may include all necessary hardware and/or secondary components to effectuate such connections. According to one aspect, saw system 10 may include a single adjustment system 80 controlling all guide roller housings 38 contained therein. According to another aspect, each individual unit, including scanning unit 12, transition unit 14, and/or cutting unit 16, may include a separate adjustment system 80 and motor 98. As shown in the figures, with particular reference to FIGS. 5A-5C, all three units may include an adjustment system 80, but with the adjustment system 80 of scanning unit 12 being controlled by the adjustment motor 98 contained within transition unit 14. According to this aspect, adjustment system 80 of cutting unit 16 may be separately controlled by a second adjustment motor 98. Further, adjustment system 80 of the scanning unit 12 and/or transition unit 14 may include additional components connecting both systems 80 to allow for control by the shared adjustment motor 98.

Guide rollers 36 may further include a plurality of pneumatic actuators 40 which may be arranged such that each guide roller 36 and arm 37 are operably connected to a pneumatic actuator 40. Each pneumatic actuator 40 may be operationally connected a pneumatic control unit 87 which may include any additional components necessary for operation of pneumatic actuators 40, such as a pneumatic switch and the like. According to one aspect, each pneumatic actuator 40 may include a dual main cylinder 82 with a first, or lower, piston 84 extending downwards therefrom and a second, or upper, piston 86 extending upwards therefrom. Alternatively, each pneumatic actuator 40 may be a dual cylinder with a first cylinder mounted on top of and operationally connected to a second cylinder. The dual arrangement of the pneumatic actuators 40 may allow the guide rollers 36 to be moved downward to contact the top face of a piece of wood 200 moving through scanning unit 12 (and saw system 10 generally). This dual arrangement may also allow the guide rollers 36 to move upwards and function as a defacto shock absorber to prevent breakage to the guide rollers 36 and other saw system 10 components by a piece of wood 200 being incorrectly fed into system 10. For example, a large thickness piece of wood 200 that is fed into system 10 without raising the guide roller housing 38 with the coarse adjustment system 80 may impact the guide rollers 36, arms 37, or other similar components. The upwards movement of guide rollers 36 facilitated by the dual arrangement of pneumatic actuators 40 may allow for such an impact to be absorbed without shearing off or otherwise damaging the guide rollers 36 and system 10 components.

According to one aspect, the psi in the upper cylinder (i.e. upper piston 86) may be slightly higher than the psi in lower cylinder (i.e. lower piston 84). However, the relative psi settings may be determined according to the desired implementation. According to this aspect, the upper piston 86 may have approximately 5-10 additional psi compared to the lower piston 84. According to another aspect, actuators 40 may be hydraulic, spring biased, spring loaded, or otherwise operated and/or controlled through any other suitable means.

Transition unit 14 may be adjacent scanning unit 12 and may include a housing 88 that is separate from but connectable to housing 22 of scanning unit 12. Transition unit 14 may further contain a third servo motor 90, a fourth servo motor 92, a plurality of rollers 31 arranged into a third roller set 94 and a fourth roller set 96, a plurality of guide rollers 36, a guide roller housing 38, a coarse adjustment system 80 and an adjustment motor 98. Transition unit 14 may also include a computer, a processor, or the like which may be in further communication with a computer or processor within scanning unit 12 and/or cutting unit 16, as discussed further herein. Various other components within transition unit 14 may be discussed further below with relation to the operation thereof.

As with scanning unit 12, transition unit 14 housing 88 may have a bottom or lower portion 100 which may contain the third and fourth servo motors 90, 92 and the third and fourth roller sets 94, 96 therein. Lower portion 100 of the housing 88 may have likewise one or more removable panels 102 and one or more handles 103 thereon to allow an operator access to the components contained therein for maintenance and the like. The housing 88 may also have a top or upper portion 104 with one or more access doors 106 to allow an operator access to the interior of the transition unit 14, including the top of the third and fourth roller sets 94, 96 and the path 198 a piece of wood 200 may take as it travels through the transition unit 14. Top portion 104 may further contain a plurality of guide rollers 36, guide roller housing 38, and pneumatic actuators 40, as discussed further below. Access door 106 may include one or more transparent panes, illustrated as window 196, which may facilitate an operators' ability to view wood 200 moving through transition unit 14 to monitor for proper operation, component positioning, maintenance concerns, or the like while safely containing the components of transition unit 14 and wood 200 therein. According to one aspect, window 196 may be constructed of any suitable transparent or partially transparent material, including glass, safety glass, plastic, acrylic, or the like. According to another aspect, window 196 may be omitted, as desired or necessary.

The separation between lower and upper portions 100, 104 of the housing 88 of the transition unit 14 may be defined by one or more plates 108, which may be substantially similar to plates 52, but for their location within transition unit 14 rather than scanning unit 12. Plates 108 may have a plurality of openings 110 defined therein that may each correspond to a roller 31. According to one aspect, unlike scanning unit 12 which utilizes two plates 56 and 56 to allow separation for the scanners 24 to operation, plate 108 may be a single plate 108 that may extend the entire longitudinal width of transition unit 14 and may have openings 110 defined therein corresponding to rollers 31 of both third and fourth roller sets 94, 96. According to another aspect, separate plates 108 may be utilized in transition unit 14 corresponding to each of third and fourth roller sets 94, 96.

The housing 88 of the transition unit 14 may have a first pass-through opening 112 defined in a first side 114 thereof and a second pass-through opening 116 defined in a second side 118 thereof. The first side 114 may be determined as the side of the transition unit 14 that is connected or otherwise adjacent to the scanning unit 12 and may therefore accept a piece of wood 200 from the scanning unit 12 while the second side 118 may be opposite thereto, as discussed below. Therefore, the first opening 112 may define the entrance 120 into the transition unit 14 for the piece of wood 200 while the second opening 116 may then define the exit 122 from the transition unit 14. Transition unit 14 may further include a portion of fence 42 extending longitudinally between first and second openings 112, 116 along the wood path 198.

The housing 88 of transition unit 14 may further include mounting points, support members, or the like for various other components as discussed previously herein. Housing 88 may further have one or more mounting points for emergency start/stop switches 20, controls 190, or the like.

Similar to first and second servo motors 28, 30, third and fourth servo motors 90, 92 may be any suitable servo type motor that is operable to drive third and fourth roller sets 94, 96. According to one aspect, third and fourth servo motors 90, 92 may be any suitable motor or actuator allowing for precise control of the rollers 31, as discussed herein. Third and fourth servo motors 90, 92 may further include one or more sensors, control modules, or the like, as necessary for operation and control thereof. According to another aspect, third and fourth servo motors 90, 92 may be any suitable for use in a closed loop system or suitable for precise control of rollers 31, as discussed herein. Third and fourth servo motors 90, 92 may each include a drive roller 33 which may interact with related drive belts (discussed more fully below) to allow third and fourth servo motors 90, 92 to interact with rollers 31 of saw system 10.

Rollers 31 of transition unit 14 may be substantially similar or identical to rollers 31 of scanning unit 12 and may be formed of any suitable material, including steel or other metals, polymers, plastics, or the like and may include a surface texture to aid in gripping or otherwise moving wood 200 along path 198 through saw system 10. Rollers 31 may be mounted in a sufficient manner as to permit them to rotate about a longitudinal axis running through each roller 31. Rollers 31 may further include a projection, extension, flange, groove, channel, or the like to permit interaction between rollers 31 and drive belts associated with each roller set and/or servo motor, as discussed herein. As mentioned previously herein, rollers 31 may or may not be identical in size, material, or the like as dictated by the desired implementation.

As with scanning unit 12, rollers 31 within transition unit 14 (and within saw system 10 generally) may be arranged in sets, e.g. third roller set 94 and fourth roller set 96. Third servo motor 90 may thus be connected to third roller set 94 via a third drive belt 124, and may further utilize one or more tensioning rollers 76 to maintain the appropriate tension on the third drive belt 124. The third roller set 94 may include one or more individual rollers 31 and may be defined by its position within saw system 10 as the roller set encountered by a piece of wood 200 as it moves into the transition unit 14 from the scanning unit 12. Specifically, third roller set 94 may be the roller set closest to the entrance 120 of transition unit 14. Similarly, the fourth servo motor 92 may be connected to the fourth roller set 96 via a fourth drive belt 126, including with one or more tensioning rollers 76. Fourth roller set 96 may likewise be defined by its position within saw system 10 as the next set of rollers 31 encountered by the piece of wood 200 after the third roller set 94, as the wood 200 moves along wood path 198 and through the saw system 10, as further discussed herein. According to one aspect, third and/or fourth roller sets 94, 96 may include at least one roller 31 and at least one tensioning roller 76, along with the associated servo motor and drive roller 33 that are all connected or controlled by a single drive belt. For example, third roller set 94 is contemplated to include one or more rollers 31, tensioning roller(s) 76, third servo motor 92, drive roller 33, and third drive belt 124 to complete a "closed system" meaning that third roller set 94 can operate independently from other roller sets, such as fourth roller set 96.

As with scanning unit 12, transition unit 14 may further include a plurality of guide rollers 36 extending at downward from a mounting unit or housing 38 towards the wood path 198 and/or rollers 31. Guide rollers 36 and guide roller housing 38 of transition unit 14 may be substantially similar or identical to guide rollers 36 and guide roller housing 38 of scanning unit 12 and are understood to be the rollers that are above the wood path 198 such that when a piece of wood 200 is present within transition unit 14, the guide rollers 36 will interact with a top surface thereof while the rollers 31 of third and fourth roller sets 94, 96 will interact with a bottom surface thereof. According to one aspect, guide rollers 36 may be numbered and positioned to have a guide roller 36 positioned vertically above each roller 31 such that when the rollers 31 and guide rollers 36 engage a piece of wood 200, the rollers 31 and guide rollers 36 are directly opposite one another on the wood 200. According to another aspect, guide rollers 36 may be spaced and positioned as needed, desired, and/or dictated by the specific implementation thereof. Guide rollers 36 may be constructed of any suitable material, including metal, plastic, polymers, or the like, and may be uniformly sized, or may vary in size and/or material according to their placement and/or role within saw system 10.

As guide rollers 36 and guide roller housing 38 of transition unit 14 are substantially similar or identical to guide rollers 36 of scanning unit 12, previously discussed herein, they will be understood to have similar or identical connections, components, functions, and operations as described previously herein. Specifically, it will be understood that guide rollers 36 and guide roller housings 38 will include the relevant components regardless of their placement within saw system 10, including, but not limited to, arms 37, coarse adjustment mechanisms 80, adjustment motors 98, pneumatic actuators 40, pneumatic control units 87, and all associated control mechanisms, support members, mounting components, hardware, and the like.

Cutting unit 16 may be adjacent transition unit 14 and may include a housing 128 that is separate from but connectable to housing 88 of transition unit 14. Cutting unit 16 may further contain a fifth servo motor 134, a sixth servo motor 136, a seventh servo motor 138, a plurality of rollers 31 arranged into a fifth roller set 140, sixth roller set 142, and a seventh roller set 144, a plurality of guide rollers 36, a guide roller housing 38, a coarse adjustment system 80, and an adjustment motor 98. Cutting unit 16 may also include a computer, a processor, or the like which may be in further communication with a computer or processor within scanning unit 12 and/or transition unit 16, as discussed further herein. Various other components within cutting unit 16 may be discussed further below with relation to the operation thereof.

Cutting unit 16 housing 128 may have a bottom or lower portion 129 which may contain fifth, sixth, and seventh servo motors 134, 136, and 138, and the fifth, sixth, and seventh roller sets 140, 142, and 144. Lower portion 129 of the housing 128 may have likewise one or more removable panels 130 and one or more handles 131 thereon to allow an operator access to the components contained therein for maintenance and the like. The housing 128 may also have a top or upper portion 132 with one or more access doors 133 to allow an operator access to the interior of the cutting unit 16, including the top of the fifth, sixth, and seventh roller sets 140, 142, and 144, and the path 198 a piece of wood 200 may take as it travels through the cutting unit 16. Top portion 132 may further contain a plurality of guide rollers 36, guide roller housing 38, and pneumatic actuators 40, as discussed further below. Access door 133 may include one or more transparent panes, illustrated as window 196, which may facilitate an operators' ability to view wood 200 moving through cutting unit 16 to monitor for proper operation, component positioning, maintenance concerns, or the like while safely containing the components of cutting unit 16 and wood 200 therein. According to one aspect, window 196 may be constructed of any suitable transparent or partially transparent material, including glass, safety glass, plastic, acrylic, or the like. According to another aspect, window 196 may be omitted, as desired or necessary.

Cutting unit 16 may further include a saw blade 146, a saw blade 146 motor 148, a blade extension mechanism 150, and one or more vacuum ports 152 connected to or in communication with a dust removal system 153. Cutting unit 16 may also include a computer, a processor, or the like which may be in further communication with a computer or processor within scanning unit 12 and/or transition unit 14 as discussed further herein.

The separation between lower and upper portions 129, 132 of the housing 128 of the cutting unit 16 may be defined by one or more plates 158, which may be substantially similar to plates 52 and/or 108, but for their location within cutting unit 16 rather than scanning unit 12 or transition unit 14. Plates 158 may have a plurality of openings 160 defined therein that may each correspond to a roller 31. According to one aspect, like plate 108 in transition unit 14, plate 158 may be a single plate 158 that may extend the entire longitudinal width of cutting unit 16 and may have openings 160 defined therein corresponding to rollers 31 of fifth, sixth, and seventh roller sets 138, 140, and 142. According to another aspect, separate plates 158 may be utilized in cutting unit 16 corresponding to one or more of fifth, sixth, and seventh roller sets 138, 140, and 142, or any suitable or desired combination thereof. Plate 158 may further have a saw blade 146 slot 162 defined therein to allow the saw blade 146 to extend therethrough, as discussed below.

The housing 128 of the cutting unit 16 may have a first pass-through opening 164 defined in a first side 166 thereof and a second pass-through opening 168 defined in a second side 170 thereof. The first side 166 may be determined as the side of the cutting unit 16 that is connected or otherwise adjacent to the transition unit 14 and may therefore accept a piece of wood 200 from the transition unit 14 while the second side 170 may be opposite thereto, as discussed below. Therefore, the first opening 164 may define the entrance 172 into the cutting unit 16 for the piece of wood 200 while the second opening 168 may then define the exit 174 from the cutting unit 16. Cutting unit 16 may further include a portion of fence 42 extending longitudinally between first and second openings 164, 168 along the wood path 198.

The housing 128 of cutting unit 16 may further include mounting points, support members, or the like for various other components as discussed previously herein. Housing 128 may further have one or more mounting points for emergency start/stop switches 20, controls 190, or the like. Likewise, housing 128 may include amounting point or mounting bracket to support one of the one or more control panels 18 thereon.

The housings 22, 88, 128 of scanning unit 12, transition unit 14, and cutting unit 16 may be constructed of any suitable material, including metals, plastics, polymers, or the like, or any suitable combination thereof.

Similar to first through fourth servo motors 28, 30, 90, and 92, fifth, sixth, and seventh servo motors 134, 136, and 138 may be any suitable servo type motor that is operable to drive fifth, sixth, and seventh roller sets 140, 142, and 144. According to one aspect, fifth, sixth, and seventh servo motors 134, 136, and 138 may be any suitable motor or actuator allowing for precise control of the rollers 31, as discussed herein. Fifth, sixth, and seventh servo motors 134, 136, and 138 may further include one or more sensors, control modules, or the like, as necessary for operation and control thereof. According to another aspect, fifth, sixth, and seventh servo motors 134, 136, and 138 may be any suitable for use in a closed loop system or suitable for precise control of rollers 31, as discussed herein. Fifth, sixth, and seventh servo motors 134, 136, and 138 may each include a drive roller 33 which may interact with related drive belts (discussed more fully below) to allow fifth, sixth, and seventh servo motors 134, 136, and 138 to interact with rollers 31 of saw system 10.

Rollers 31 of cutting unit 16 may be substantially similar or identical to rollers 31 of scanning unit 12 and/or transition unit 14 and may be formed of any suitable material, including steel or other metals, polymers, plastics, or the like and may include a surface texture to aid in gripping or otherwise moving wood 200 along path 198 through saw system 10. Rollers 31 may be mounted in a sufficient manner as to permit them to rotate about a longitudinal axis running through each roller 31. Rollers 31 may further include a projection, extension, flange, groove, channel, or the like to permit interaction between rollers 31 and drive belts associated with each roller set and/or servo motor, as discussed herein. As mentioned previously herein, rollers 31 may or may not be identical in size, material, or the like as dictated by the desired implementation.

Rollers 31 within cutting unit 16 (and within saw system 10 generally) may similarly be arranged in sets, e.g. fifth roller set 140, sixth roller set 142, and seventh roller set 144. Fifth servo motor 134 may thus be connected to fifth roller set 140 via a fifth drive belt 176, and may further utilize one or more tensioning rollers 76 to maintain the appropriate tension on the fifth drive belt 176. The fifth roller set 140 may include one or more individual rollers 31 and may be defined by its position within saw system 10 as the roller set encountered by a piece of wood 200 as it moves into the cutting unit 16 from the transition unit 14. Specifically, fifth roller set 140 may be the roller set closest to the entrance 172 of cutting unit 16. Similarly, the sixth servo motor 136 may be connected to the sixth roller set 142 via a sixth drive belt 178, including with one or more tensioning rollers 76. Sixth roller set 142 may likewise be defined by its position within saw system 10 as the next set of rollers 31 encountered by the piece of wood 200 after the fifth roller set 140, and immediately before being cut by saw blade 146, as further discussed herein. Seventh servo motor 138 may be connected to the seventh roller set 144 via a seventh drive belt 180, including with one or more tensioning rollers 76. Seventh roller set 144 may likewise be defined by its position within saw system 10 as the next set of rollers 31 encountered by the piece of wood 200 after the sixth roller set 142, and immediately after being cut by saw blade 146. According to one aspect, fifth, sixth, and/or seventh roller sets 140, 142, and 144 may include at least one roller 31 and at least one tensioning roller 76, along with the associated servo motor and drive roller 33 that are all connected or controlled by a single drive belt. For example, fifth roller set 140 is contemplated to include one or more rollers 31, tensioning roller(s) 76, fifth servo motor 134, drive roller 33, and fifth drive belt 176 to complete a "closed system" meaning that fifth roller set 140 can operate independently from other roller sets, such as sixth roller set 142.

Cutting unit 16 may employ additional exit rollers 25 which may be substantially similar to rollers 31 in construction, form, and mounting, however, they may vary in that exit rollers 35 may be free of a connection to any of the servo motors such that they are unpowered. Exit rollers 35 may be mounted exterior of cutting unit 16 exit 174 and may be operable to provide a "roll off" area for wood 200 that has been cut and is exiting the cutting unit 16.

As with scanning unit 12 and transition unit 14, cutting unit 16 may further include a plurality of guide rollers 36 extending at downward from a mounting unit or housing 38 towards the wood path 198 and/or rollers 31. Guide rollers 36 and guide roller housing 38 of cutting unit 16 may be substantially similar or identical to guide rollers 36 and guide roller housing 38 of scanning unit 12 and/or transition unit 14 and are understood to be the rollers that are above the wood path 198 such that when a piece of wood 200 is present within cutting unit 16, the guide rollers 36 will interact with a top surface thereof while the rollers 31 of third and fourth roller sets 94, 96 will interact with a bottom surface thereof. According to one aspect, guide rollers 36 may be numbered and positioned to have a guide roller 36 positioned vertically above each roller 31 such that when the rollers 31 and guide rollers 36 engage a piece of wood 200, the rollers 31 and guide rollers 36 are directly opposite one another on the wood 200. According to another aspect, guide rollers 36 may be spaced and positioned as needed, desired, and/or dictated by the specific implementation thereof. Guide rollers 36 may be constructed of any suitable material, including metal, plastic, polymers, or the like, and may be uniformly sized, or may vary in size and/or material according to their placement and/or role within saw system 10.

As guide rollers 36 and guide roller housing 38 of cutting unit 16 are substantially similar or identical to guide rollers 36 of scanning unit 12 and transition unit 14, previously discussed herein, they will be understood to have similar or identical connections, components, functions, and operations as described previously herein. Specifically, it will be understood that guide rollers 36 and guide roller housings 38 will include the relevant components regardless of their placement within saw system 10, including, but not limited to, arms 37, coarse adjustment mechanisms 80, adjustment motors 98, pneumatic actuators 40, pneumatic control units 87, and all associated control mechanisms, support members, mounting components, hardware, and the like.

Figure 5A:
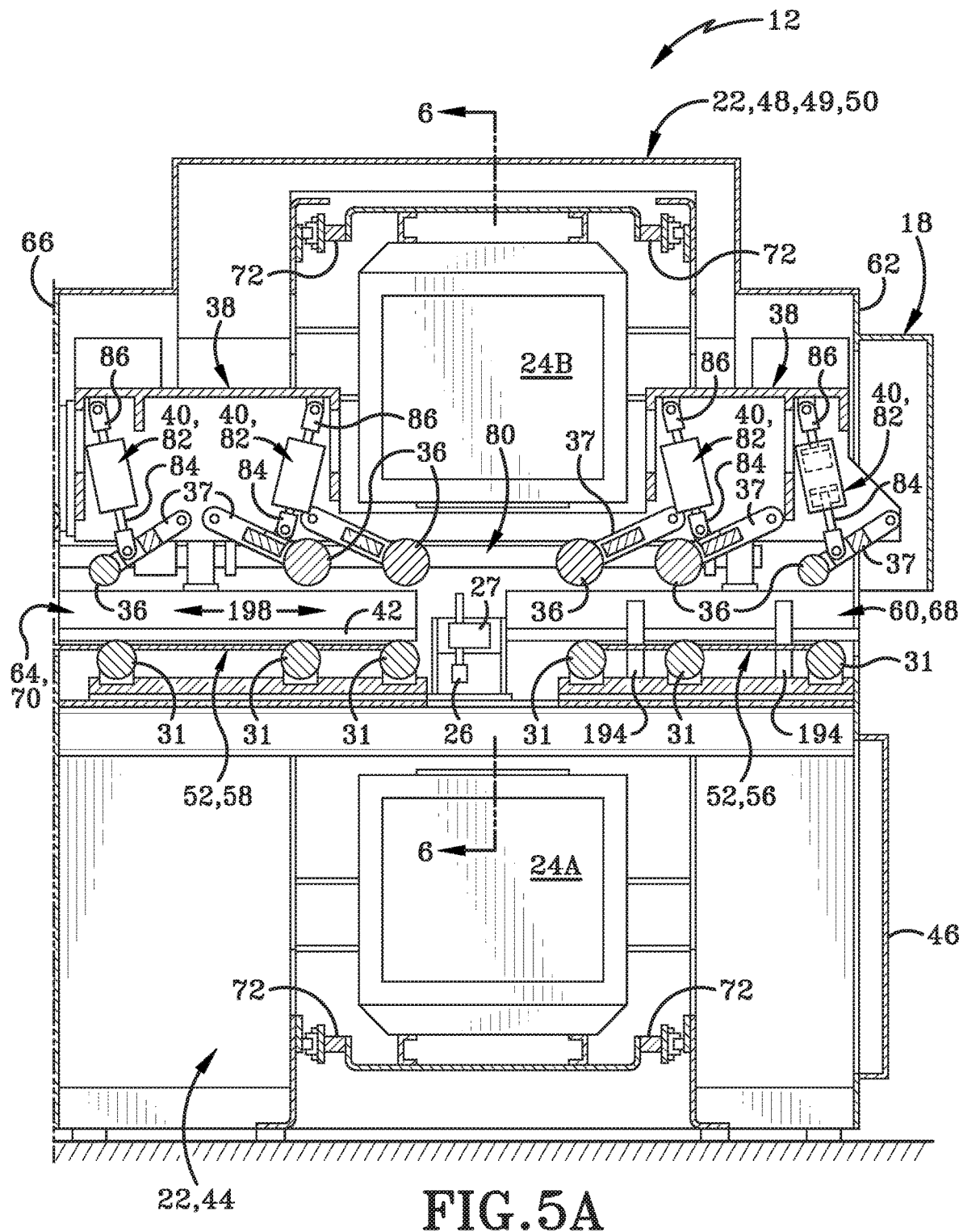
FIG. 5A is a second front elevation cross sectional view of a scanning unit of an automated saw system taken along line 5-5 indicated in FIG. 3, according to one aspect of the present disclosure.
Figure 5B:
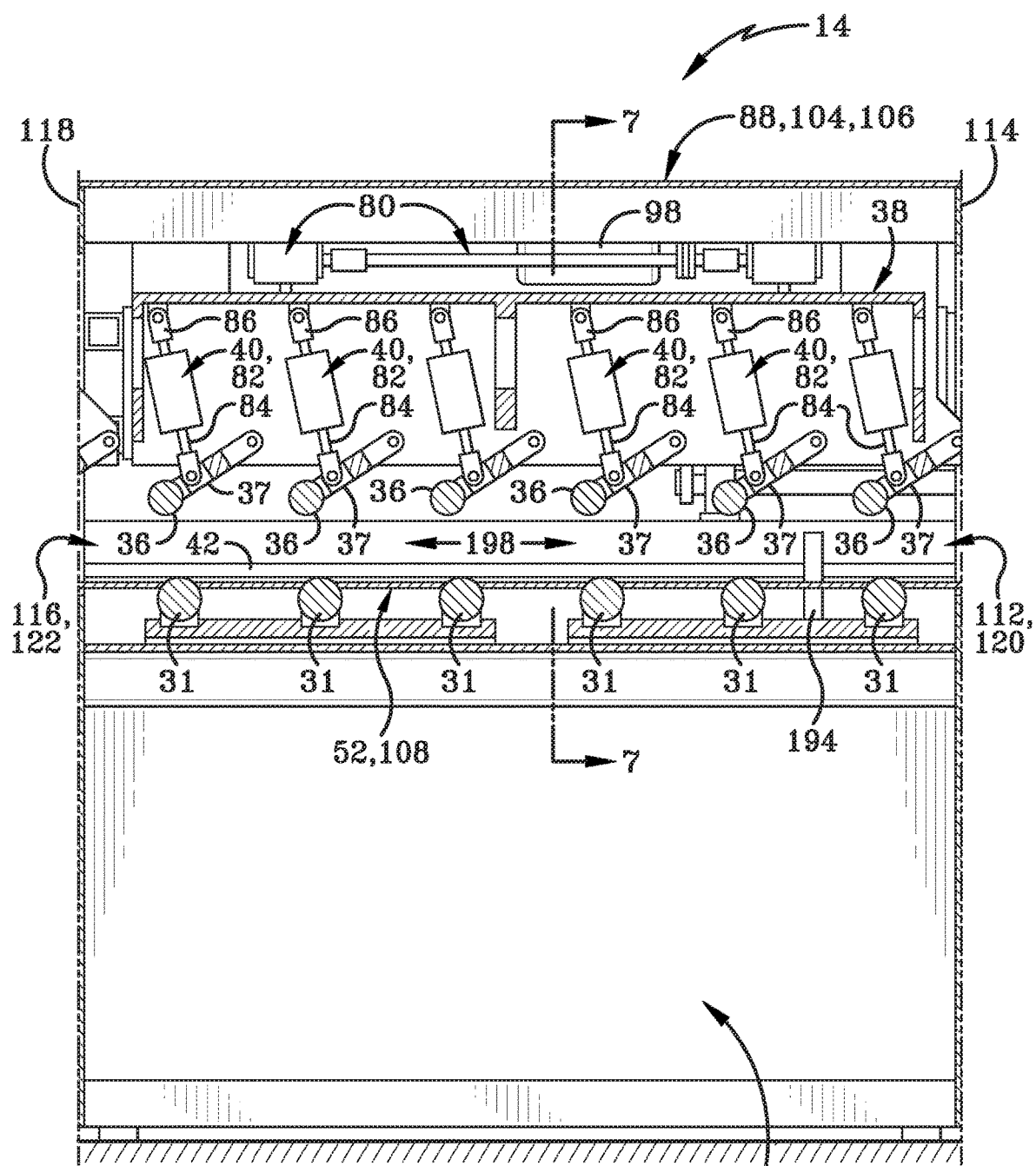
FIG. 5B is a second front elevation cross sectional view of a transition unit of an automated saw system taken along line 5-5 indicated in FIG. 3, according to one aspect of the present disclosure.
Figure 5C:
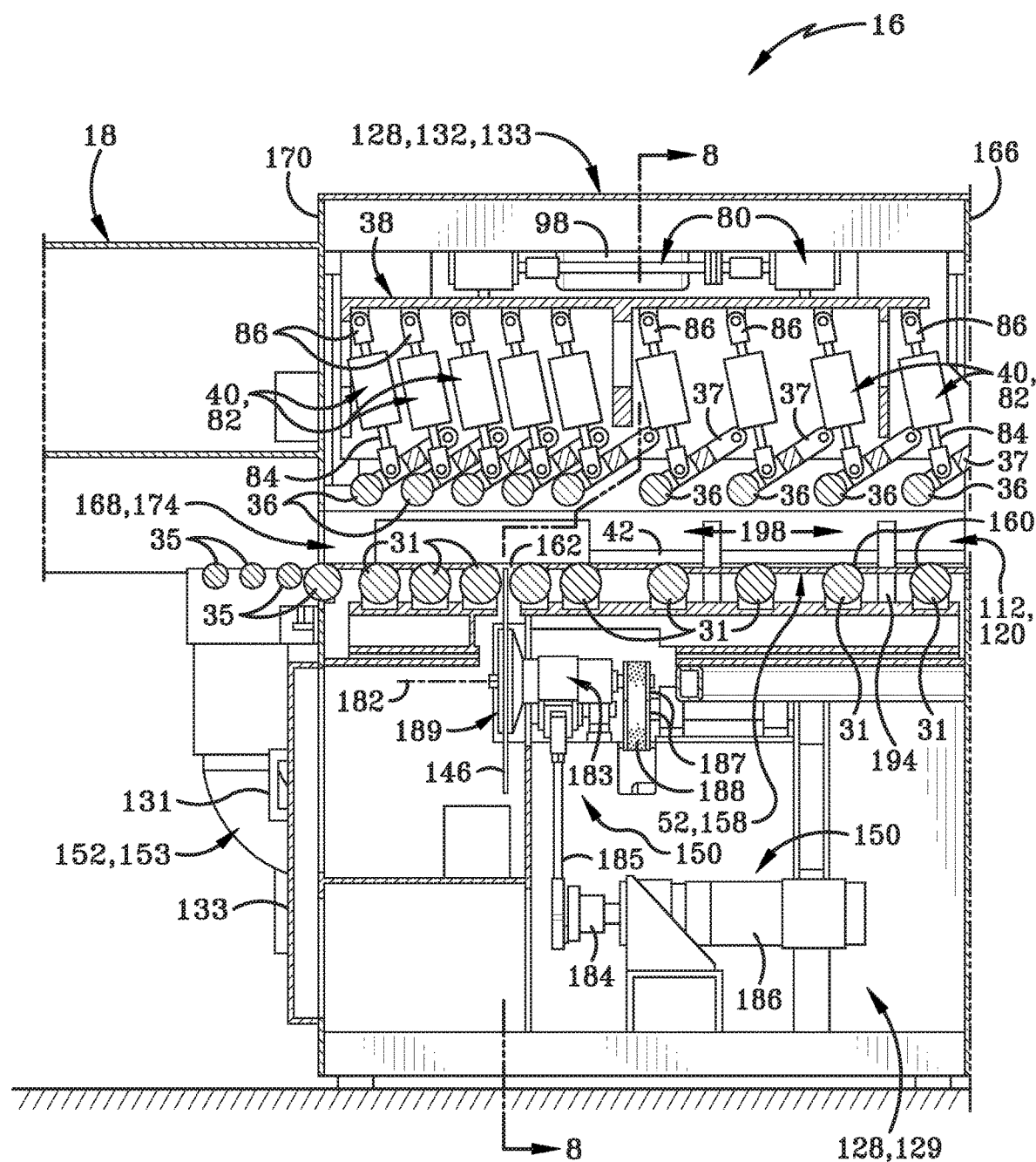
FIG. 5C is a second front elevation cross sectional view of a cutting unit of an automated saw system taken along line 5-5 indicated in FIG. 3, according to one aspect of the present disclosure.
Figure 6:
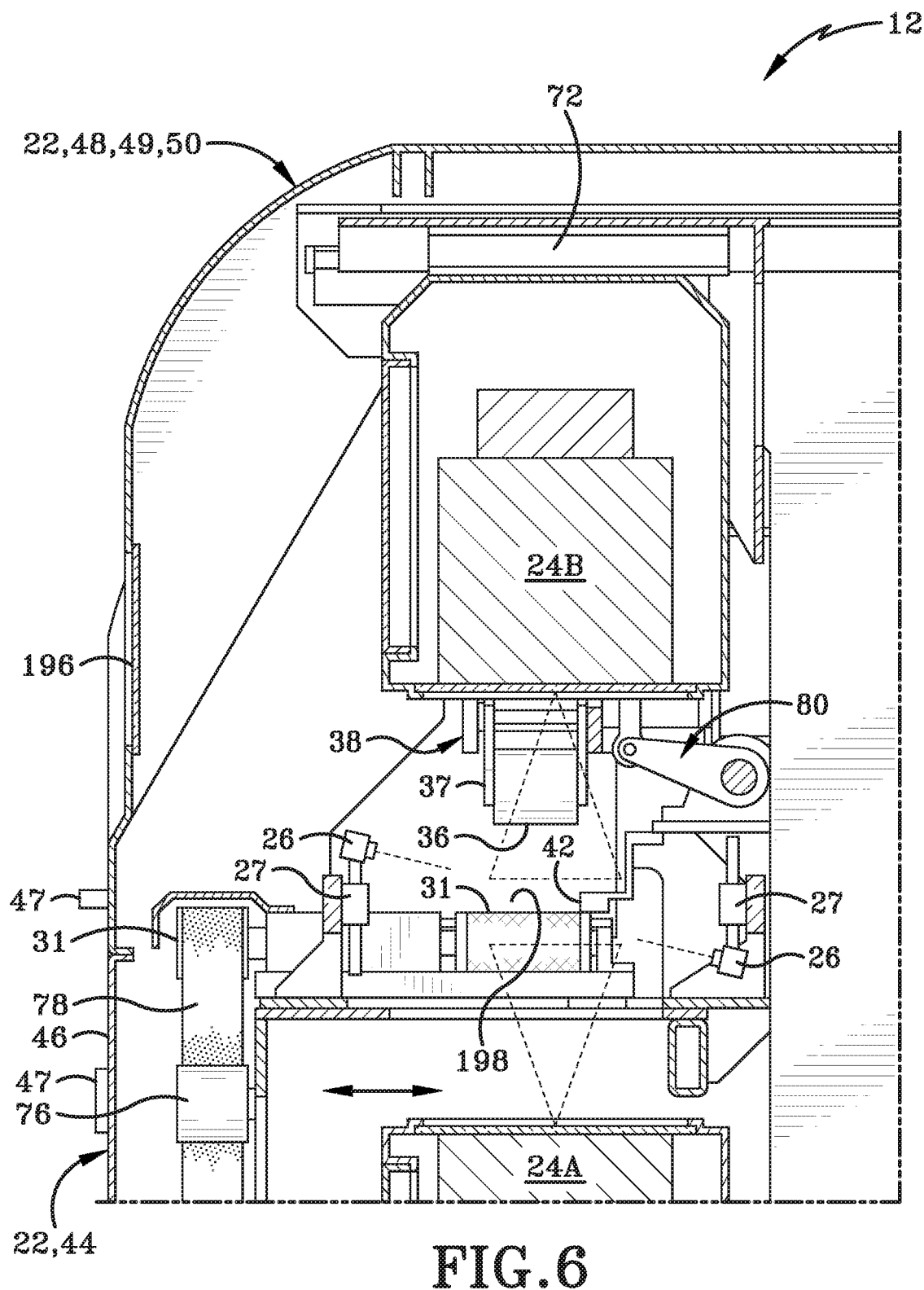
FIG. 6 is a right side elevation cross sectional view of a scanning unit of an automated saw system taken along line 6-6 indicated in FIG. 5A, according to one aspect of the present disclosure.
Figure 7:
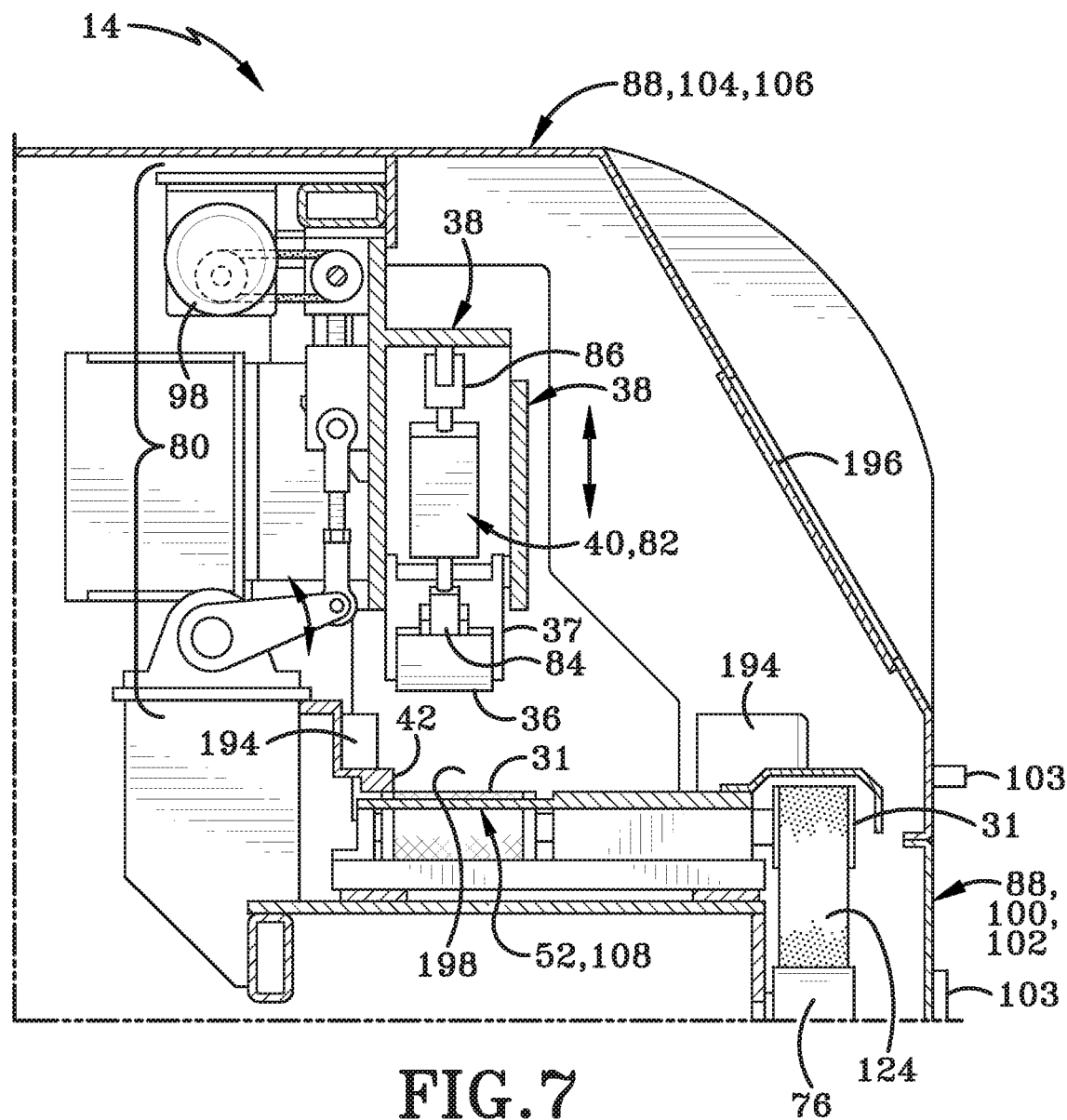
FIG. 7 is a left side elevation cross sectional view of a transition unit of an automated saw system taken along line 7-7 indicated in FIG. 5B, according to one aspect of the present disclosure.
Figure 8:
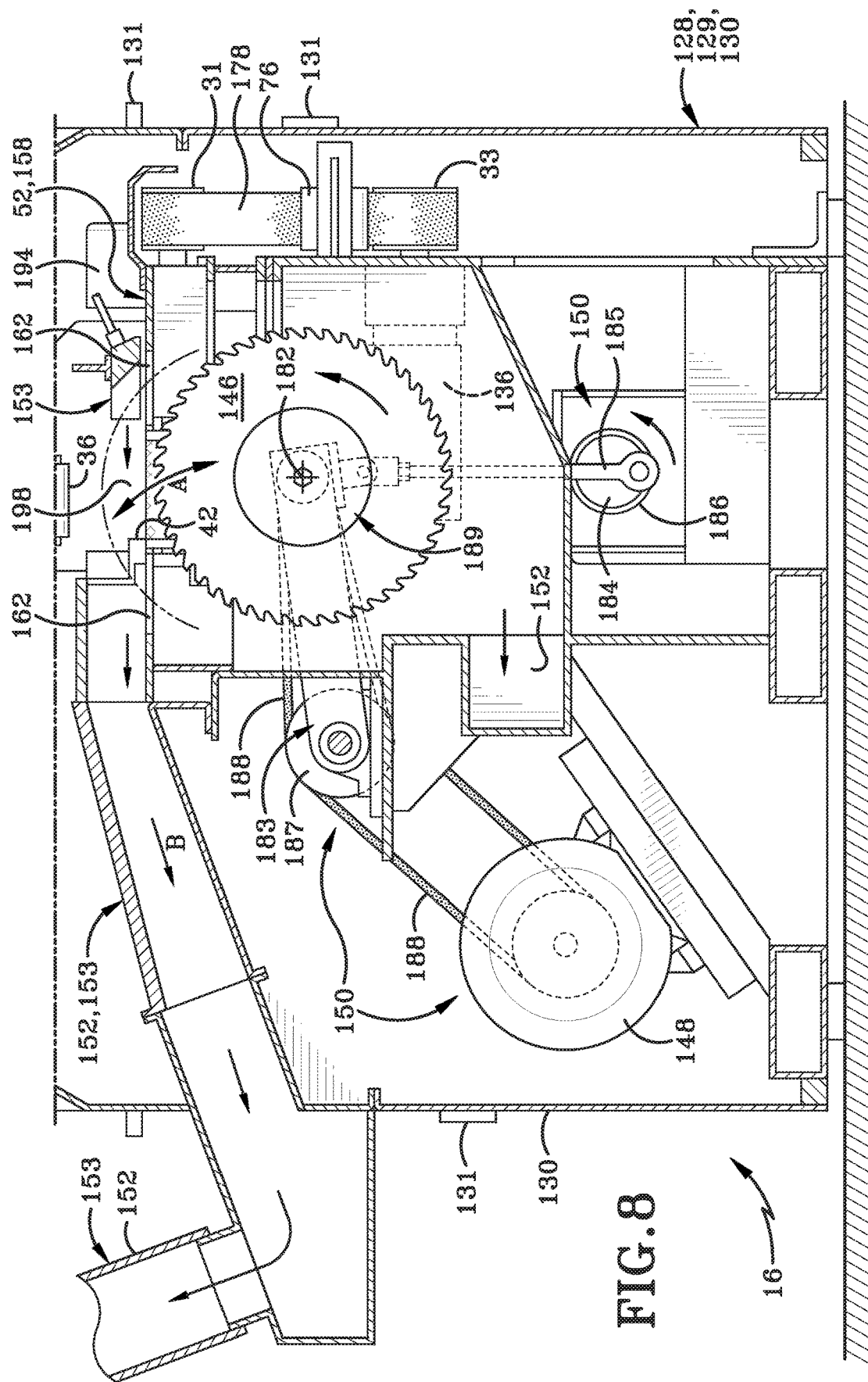
FIG. 8 is a left side elevation cross sectional view of a cutting unit of an automated saw system taken along line 8-8 indicated in FIG. 5C, according to one aspect of the present disclosure.
Figure 9B:
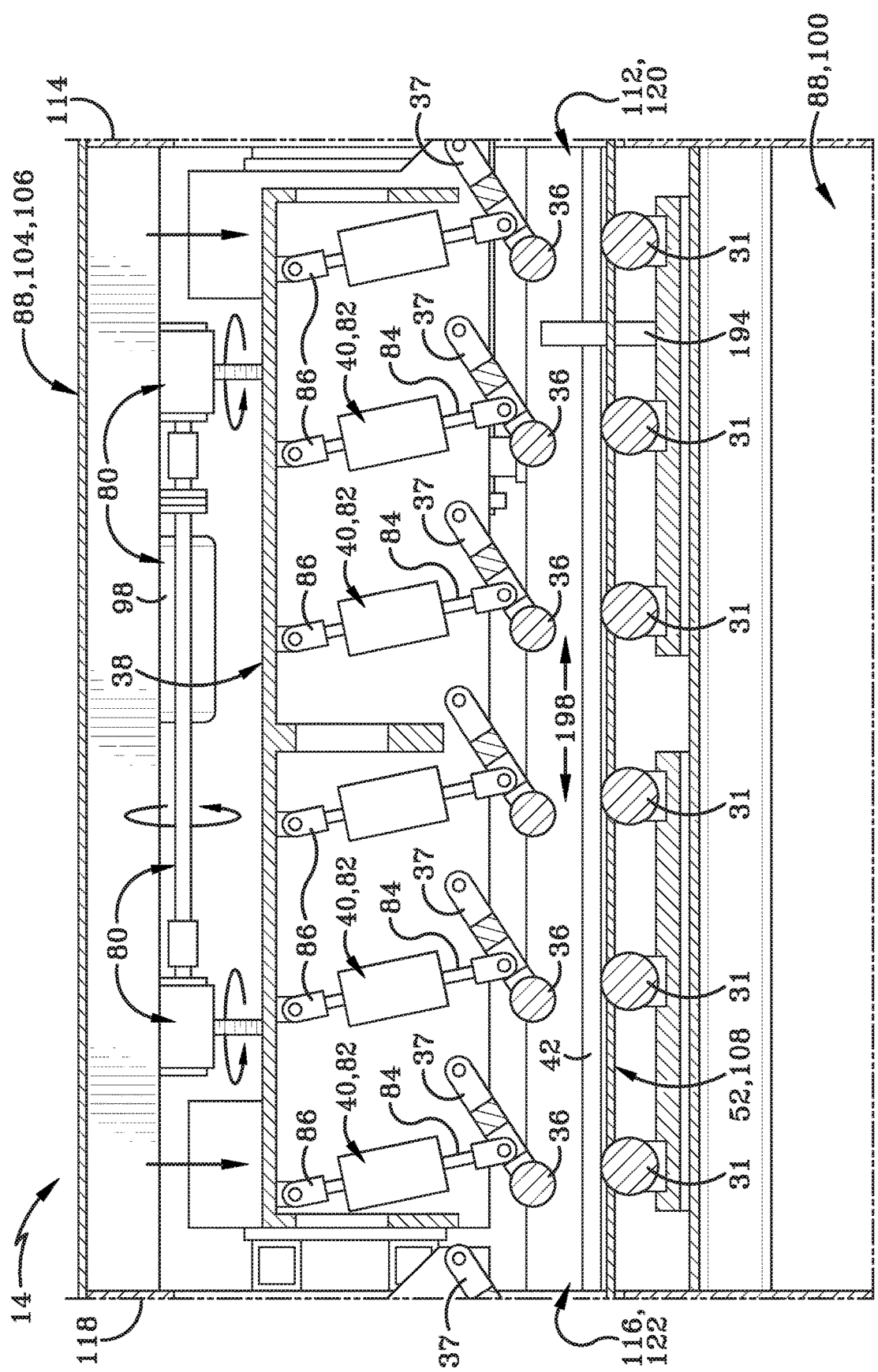
FIG. 9B is a close up front elevation cross sectional view of the transition unit of an automated saw system from FIG. 5B, according to one aspect of the present disclosure.
Figure 10:
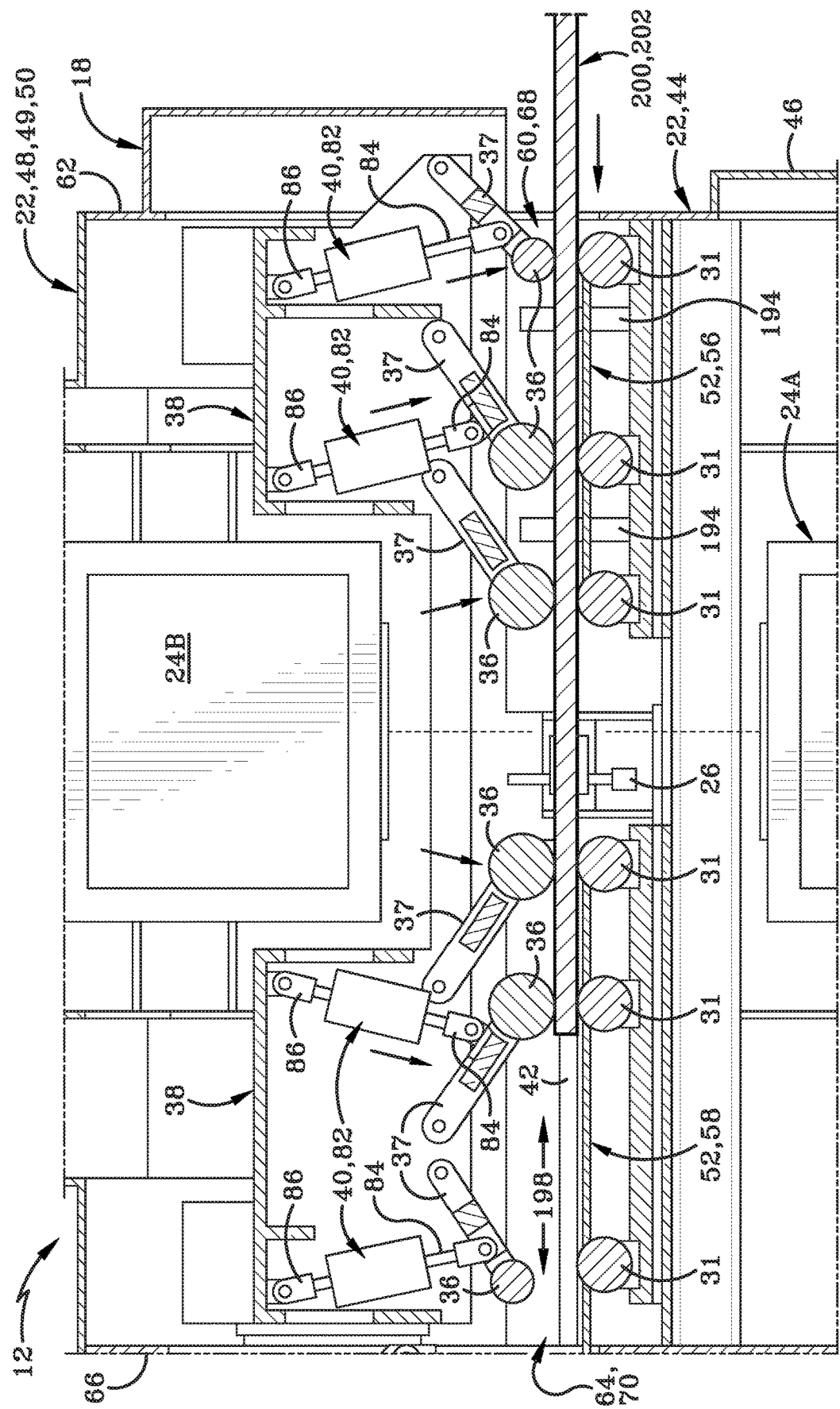
FIG. 10 is an operational front elevation cross sectional view showing a board to be cut entering the scanning unit of an automated saw system from FIG. 9A, according to one aspect of the present disclosure.

Saw blade 146 may be a standard crosscut saw blade 146 of suitable size and teeth count to perform high speed wood cutting. The specific saw blade 146 type, material, teeth count, and size may vary depending on the desired implementation of the present saw system 10. Saw blade 146 may be mounted to the blade extension mechanism 150 via a blade mount 189, which may be any suitable blade mounting system operable to secure the saw blade 146 to the blade extension mechanism 150. According to one aspect, blade mount 159 may include a central mounting point that may define an axis of rotation for saw blade 146. This axis of rotation is best seen in FIG. 5C as axis 182.

Saw blade 146 may be aligned with blade slot 162 defined in plate 158 between the sixth and seventh roller sets 142, 144 such that a piece of wood 200 to be cut moving through cutting unit 16 may extend over blade slot 162 and may be engaged with at least one roller 31 of sixth and seventh roller sets 142, 144 while saw blade 146 is raised up through blade slot 162 to engage and cut the wood 200, as discussed below.

The saw blade 146 may be operated via a separate drive system including a blade motor 148 that may drive saw blade 146 through the operation of one or more pulleys 187 and belts 188 within the lower portion 129 of housing 128 of cutting unit 16. According to one aspect, pulleys 187 and belts 188 may be replaced with any suitable comparable components, including, but not limited to, direct drive systems, chains, or the like. Saw blade 146 motor 148 may be any suitable motor operable to cause saw blade 146 to rotate about axis 182. As discussed below, saw blade 146 may need to be rapidly spun up to speed and/or rapidly stopped so saw blade 146 motor 168 is understood to be of sufficient size and power to deliver sufficient torque to allow for rapid starting and stopping of saw blade 146's 146 rotation.

Blade extension mechanism 150 may be any suitable mechanism operable to raise and lower saw blade 146 through the blade slot 162 to cut a piece of wood 200 that is in the cutting unit 16. According to one aspect, blade extension mechanism 150 may include one or more arms 183 which may pivot to move blade 146 upwards or downwards as desired. Arms 183 may be operable through the use of a cam or wheel 183 and a rod 184 combination to move arms 183 via an extension motor 186. According to another aspect, blade extension mechanism 150 may be a pneumatic or a hydraulic actuator, or other similar device. The specific blade extension mechanism 150 may vary depending on the saw blade 146 size, speed, and the like. Other variables that may influence the specific blade extension mechanism 150 may include the wood type, thickness, width, density, and the like. According to another aspect, blade extension mechanism 150 may operate at variable speeds and may be sped up or slowed down as necessary, as discussed below.

It will be understood that both blade extension mechanism 150 and drive system may include any additional components as needed for proper installation and operation thereof, including support members, mounting structures, hardware, bearings, pistons, or the like.

Automated saw system 10 may further include one or more control panels 18 having one or more controls 190 operationally connected thereto. According to one aspect, a control panel 18 may be connected to the housing 128 of the cutting unit 16. According to another aspect, a control panel 18 may be connected to the housing 22 of the scanning unit 12. According to another aspect, control panel 18 may be separate from but in communication with the automated saw system 10 as discussed further herein. Control panels 18 may include a display 192 which may be interactive, such as a touch screen or the like. Alternatively, control panel 18 may have a display 192 which is not interactive, but is operable to display at least one of the status and/or settings of the saw system 10 during operation. As discussed below, control panel 18 may further allow an operator to preset the specific defects or flaws that saw system 10 will scan for and/or remove from a piece of wood 200. Control panel 18 may also allow user to preset a cut list to provide boards cut to desired lengths for the chosen purpose.

Each of scanning unit 12, transition unit 14, and cutting unit 16 may be combined into a single linear saw system 10 wherein the housings 22, 88, 128 of each particular unit may be joined or otherwise connected. According to one aspect, the automated saw system 10 may have a singular housing containing all components of the scanning unit 12, the transition unit 14, and the cutting unit 16 therein. Where saw system 10 is realized with a single housing, various parts and components may be omitted or modified to accommodate the specific arrangement. For example, when housings 22, 88, and/or 128 are realized as a single continuous housing, interior sides, such as second side 66 of scanning unit 12 housing 22 and first side 114 of transition unit 14 housing 88 may be combined or omitted all together. According to another aspect, the saw system 10 may be modular and units may be added or removed as desired for the particular implementation. For example, where desirable, a second transition unit 14 may be installed between the first transition unit 14 and one of the other units.

The entrances 68, 120, 172 and exits 70, 122, 174 of each unit may be aligned when the housings of each unit are joined or otherwise connected such that the openings in and out of each unit may further define the path 198 through the saw system 10 taken by a piece of wood 200 passing therethrough. This path 198 may be linear and may extend the entire longitudinal length of saw system 10. The wood path 198 may be bounded on the bottom side by rollers 31 and plates 52, 108, 158, on the top side by guide rollers 36, and on the back edge by fence 42 to maintain the piece of wood 200 within path 198 at the desired and correct orientation as the wood 200 moves through system 10.

The wood path 198 defined through saw system 10 may have a width suitable to accept wood 200 of varying widths. According to one aspect, wood path may be approximately 12 inches wide. According to another aspect, it may be any suitable width as desired for the particular implementation. According to another aspect, the width of wood path 198 may be variable to accept wood 200 of different sizes. Further according to this aspect, the width of path 198 may be adjusted manually or automatically, and system 10 may include all necessary components to effectuate such an adjustment, as dictated by the desired implementation.

As discussed above, first through seventh servo motors 28, 30, 90, 92, 134, 136, and 138 may be any suitable servo type motor that is operable to drive the rollers 31 of each respective roller set 32, 34, 94, 96, 140, 142, and 144. According to one aspect, first through seventh servo motors 28, 30, 90, 92, 134, 136, and 138 may be electrical servo motors, hydraulic servo motors, or any other suitable servo motors as dictated by the desired implementation. While first through seventh servo motors 28, 30, 90, 92, 134, 136, and 138 are further discussed above as connected to each respective roller set 32, 34, 94, 96, 140, 142, and 144 via a drive belt 74, 78, 124, 126, 176, 178, and 180, it will be understood that any suitable connection may be used. According to one aspect, servo motors may be connected to the rollers 31 via a drive belt, drive chain, serpentine belt, through a series of belts or chains, or through any other suitable means. First through seventh servo motors 28, 30, 90, 92, 134, 136, and 138 may be controlled by a singular computer or a set of computers, processors, and/or logics and/or logic controllers 31 as discussed further herein. First through seventh servo motors 28, 30, 90, 92, 134, 136, and 138 may be synchronous or asynchronous, meaning that they may be controlled to operate in unison, or may alternatively be controlled to operate individually. According to one aspect, as discussed below, servo motors 28, 30, 90, 92, 134, 136, and 138 may be operated to be both synchronous and asynchronous as necessary.

Each of scanning unit 12, transition unit 14, cutting unit 16, and/or control panels 18 may include or be in communication with one or more computers, processors (hereinafter referred to generally as "computers"). These computers may be contained within each unit or may be remote therefrom and may be in communication with control modules or control processors with saw system 10. According to one aspect, each unit may have a dedicated computer that may control the components therein, and may be in communication with the computers in each other unit. According to another aspect, saw system 10 may have centralized computer that may control all components thereof. It will be understood that the number, placement, type, and operating system employed by computers within saw system 10 may vary depending upon the desired implementation and the desired operation thereof.

Saw system 10 may further employ one or more sensors, shown in the figures generally at reference 194. These sensors 194 may serve multiple roles and may therefore be any suitable type of sensor 194, including proximity sensors, presence sensors, timing sensors, or the like or any suitable combination thereof. According to one aspect, saw system 10 may include multiple types of sensors that may control various components therein while other sensors may provide feedback to the operator regarding various parameters. For example, one type of sensor 194 contemplated for use in saw system 10 may be a timing sensor 194 that may trigger the movement of guide rollers 36 and/or guide roller housing 38 as the leading or trailing edge of a piece of wood 200 passes a specific point within path 198. Another example of a sensor may be a simple counter that may keep a running total of factors such as operation time, the number of boards cut, or the like. It will be understood that sensors 194 may be employed as desired and may include any necessary components for the proper installation and operation thereof.

Having thus described the various components and elements of automated saw system 10, the operation and method of use therefor will now be discussed.

Automated saw system 10 may be utilized in woodworking and is contemplated to be of use in the manufacturing of wood planks, boards, panels, or other wood products having a length. For example, saw system 10 may be utilized to produce high-quality wood boards for use in hardwood flooring, fine furniture construction, and trim pieces, such as baseboards, crown molding, and the like. Saw system 10 may further utilize the scanning unit 12 in conjunction with the cutting unit 16 to remove defects and flaws from a piece of wood 200 as it passes through saw system 10 while simultaneously optimizing the wood usage to maximize the usable wood and to reduce waste.

Although saw system 10 is discussed herein for use with wood and wood products, it will be understood that other materials having a length that are desired to be cut may also be processed with saw system 10. For example, saw system 10 may be adapted to cut plastics, metal, paper products, such as cardboard, or other materials.

Current automated saw systems 10 may utilize similar scanning and automated cutting as described previously herein; however, previous automated systems typically involve a multiple queue, multiple feeder setup wherein a piece of wood 200 is first supplied to a first feeder where it is queued before being fed through an optical scanner (such as scanner 24) one board at a time. After each board is scanned in its entirety, it is then deposited on to a second feeder and enters a second queue behind the optical scanner and ahead of the crosscut saw. These current systems can be large and unwieldy and take up a significant amount of floor space in a facility, thus limiting the number of units that can be used or further limiting space for other necessary components, such as sorters, bundlers, and the like. Further, any time a piece of wood in a current system that has already been scanned is removed, reoriented on the feeder, or is otherwise damaged between the scanner and the saw, the secondary queue needs to be cleared and each piece of wood waiting in the queue must be removed and rescanned, thus causing significant down time for the system and increased effort to scan multiple pieces multiple times prior to cutting.

Again, as current scanners require the entire board to be scanned prior to cutting, the secondary queue can become backed up or overrun as multiple boards are scanned. Thus, it is common to have multiple saws behind each scanner, however, each saw must have its own queue, thus increasing the space needed and further introducing opportunities for boards to be removed, damaged, or reoriented, which further require the queue to be cleared.

In another instance, when a long length board (longer than the feeder is wide, for example) is to be scanned, the current systems may need to be supplemented with manual labor in that the board must first be scanned in its entirety and then manually moved to the saw for cutting. To maintain proper order and to maintain the queue, this may happen in one of two ways. First, the secondary queue may be cleared with no wood being scanned and added to the second feeder and once the secondary queue is cleared, the longer board may be fed through the scanner and immediately moved to the saw. This is disadvantageous as it takes the scanner offline while the secondary queue is being cleared and no boards are being produced, thus causing a delay in production. The second alternative is to insert the longer board through the scanner and then manually maintain its position within the queue. However, this is also disadvantageous as first it requires careful manual oversight of the queue to ensure that no boards being scanned and moved to the secondary queue get out of position, and second, it is potentially dangerous to the manual operators as the machines are continuing to operate while they are manually manipulating a length of board thereon and therefore putting themselves into danger for injuries from the moving parts of the feeder and/or saw elements.

Alternatively, when a board of significant length needs to be cut, it may be trimmed prior to being added to the queue to alleviate the issues above; however, trimming the board may result in one or more misaligned cuts. For example, trimming the board to fit the machine without taking into account the flaws and defects therein may result in a misplaced or a less than ideally placed cut from the automated saw to remove a defect, which may then render the remaining pieces of such a board too short or otherwise unfit for the desired end product. This may then increase the waste from a current system. This procedure therefore places a practical limitation on the maximum length of a board and may eliminate current systems from use in handling longer length wood products and/or stock.

Figure 11B:
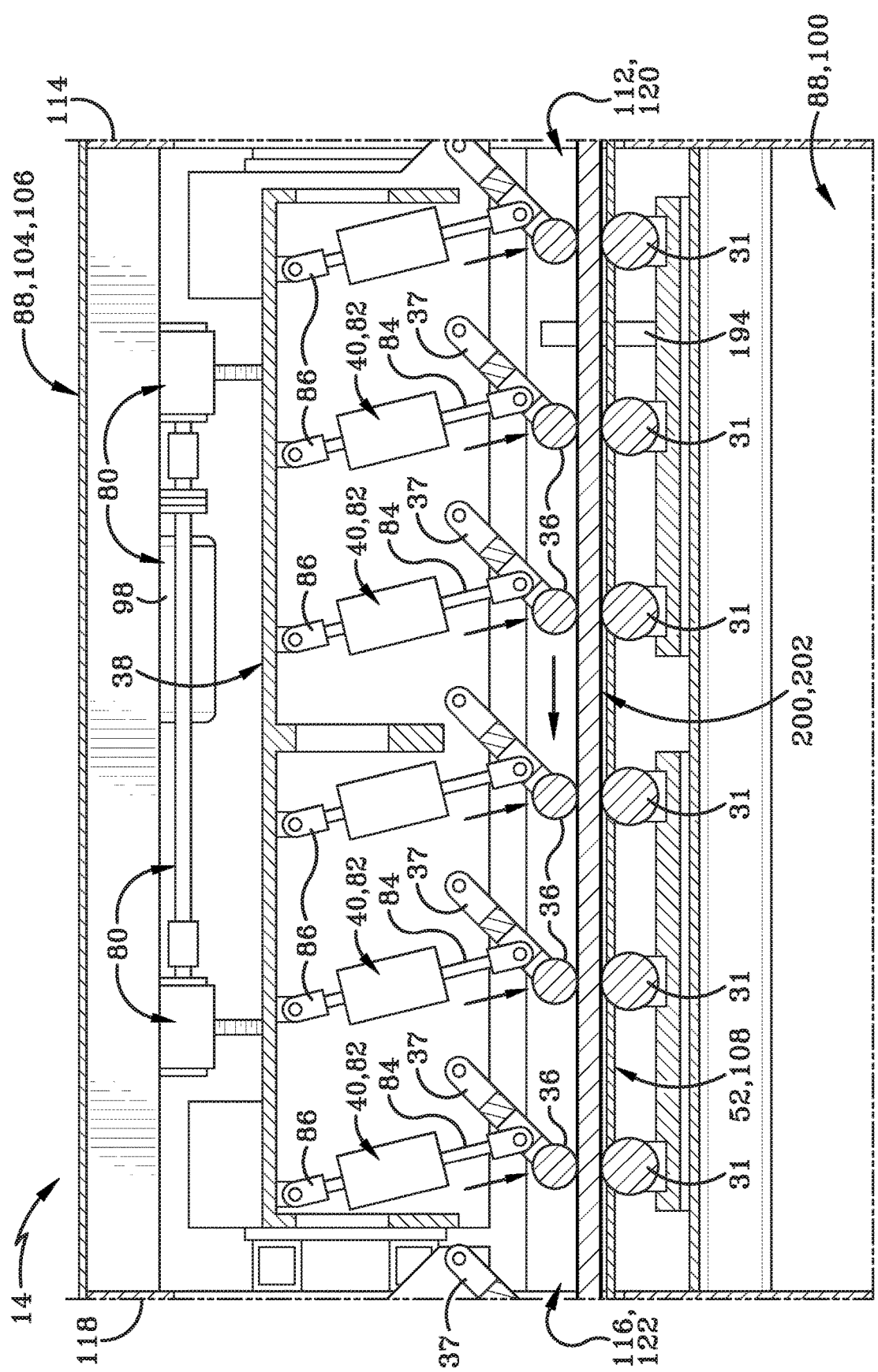
FIG. 11B is an operational front elevation cross sectional view showing a first board to be cut moving through the transition unit of an automated saw system from FIG. 9B, according to one aspect of the present disclosure.
Figure 12A:
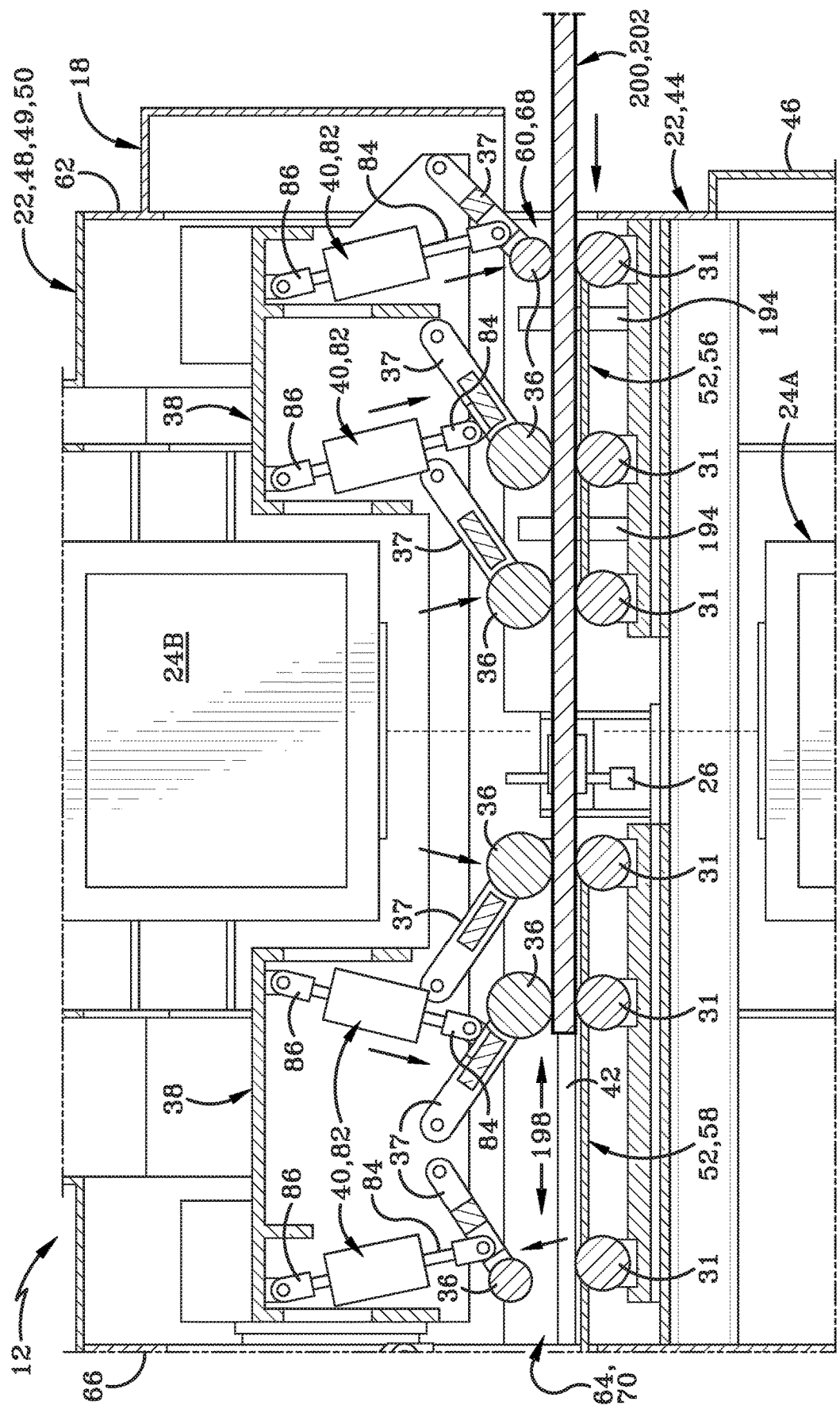
FIG. 12A is an operational front elevation cross sectional view showing a second board to be cut entering the scanning unit of an automated saw system from FIG. 11A, according to one aspect of the present disclosure.
Figure 12B:
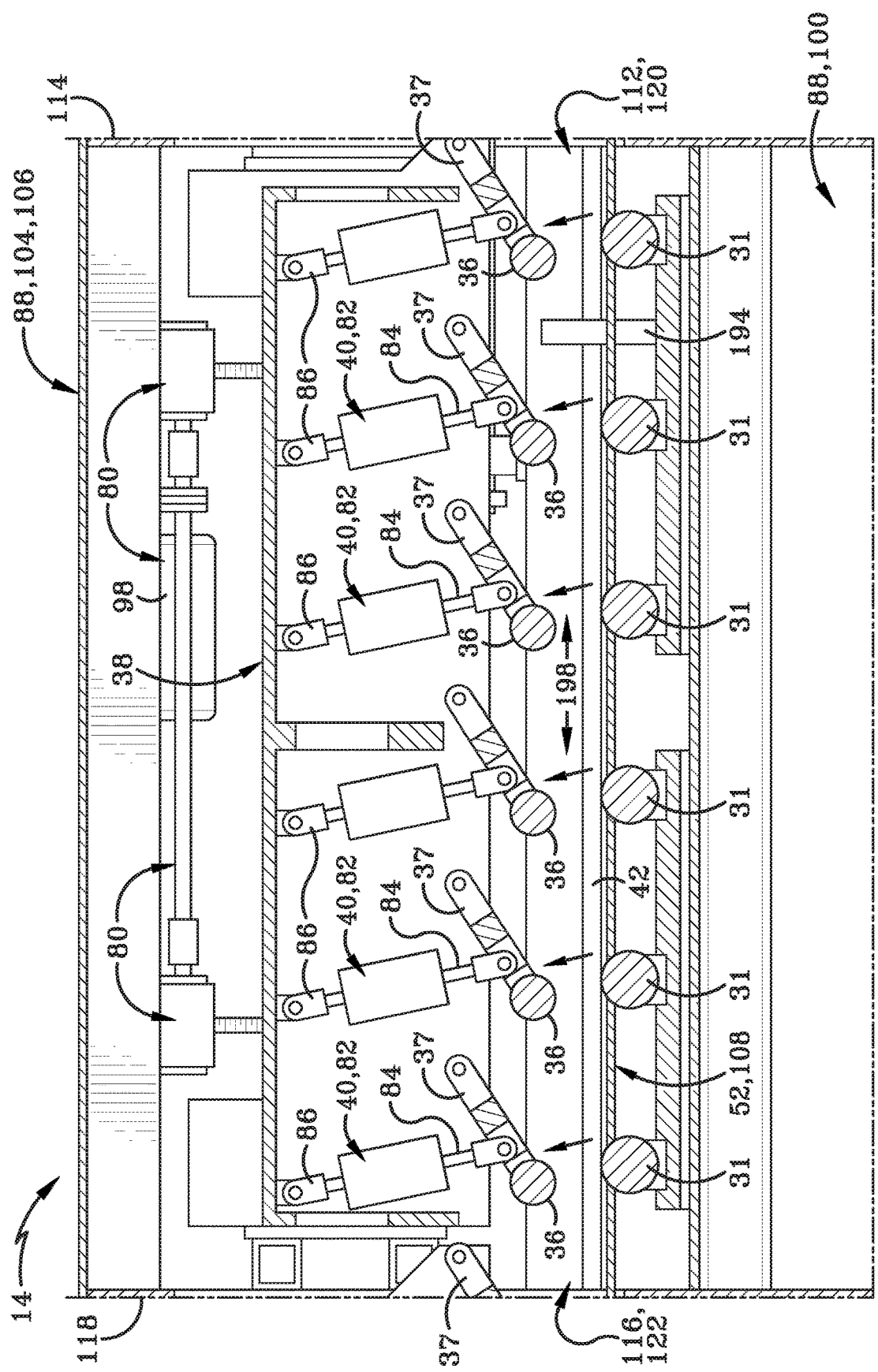
FIG. 12B is an operational front elevation cross sectional view showing the transition unit of an automated saw system from FIG. 11B after the first board to be cut has moved through but before the second board to be cut has entered, according to one aspect of the present disclosure.
Figure 12C:
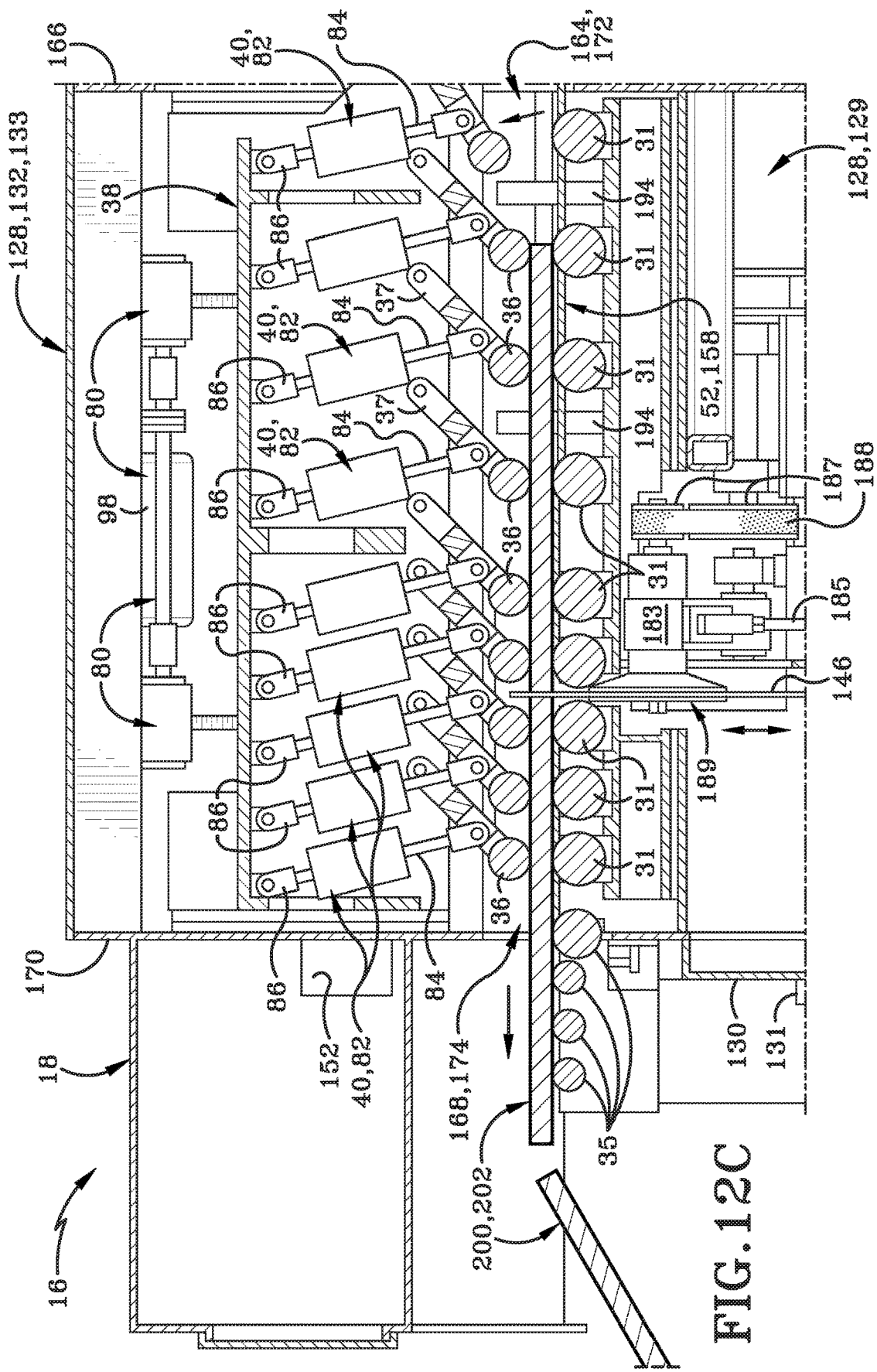
FIG. 12C (FIG. 12C) is an operational front elevation cross sectional view showing the first board to be cut moving through and being cut by the cutting unit of an automated saw system from FIG. 11C, according to one aspect of the present disclosure.

Contrast this with the automated saw system 10 of the present disclosure and the advantages provided therefrom are readily apparent. Specifically, with relation to the secondary queue, the present automated saw system 10 eliminates the secondary feeder and queue. Thus the board being scanned is either the board being cut or is the next board in line to be cut. In other words, there is no queue between the scanner and the saw. Instead the saw is always cutting the same board being simultaneously scanned (as illustrated in FIGS. 11A-11C) or the board being scanned is the next board to be cut (as illustrated in FIGS. 12A-12C). Accordingly, the scanning unit 12 need not create a series of scan files, instead it may communicate with the cutting unit 16 in real time to direct the cuts as each board passes through the saw system 10. This may significantly reduce or eliminate errors in which the queue must be cleared and each board must be rescanned by maintaining this continuous operation as long as boards are fed into the system 10. Further, as scanning unit 12, transition unit 14, and cutting unit 16 are fully enclosed and the wood path 198 therethrough is linear, there is less chance or less opportunity for wood 200 to become dislodged, disoriented, displaced, or otherwise removed from the system unless the system is stopped and the wood 200 is intentionally removed, such as for safety, maintenance, or the like. Additionally, the elimination of the secondary queue results in a smaller, more adaptable system that may reduce the floor space necessary for installation and operation of the present system 10.

To better illustrate the operation of saw system 10 of the present disclosure, an exemplary method will now be described using the example of a single piece of wood 200 moving through the saw system 10 from start to finish. For purposes of this example, the exemplary piece of wood 200 will be referred to as "the board" 202 and each step will be described in detail with reference to what is being done to or with the board 202 as it moves through the saw system 10.

First, the board 202 may be taken from a stockpile or storage location and placed onto a feeder, not unlike the types of feeders used in prior art systems, which may queue the board 202 before moving it into the scanning unit 12 of the saw system 10. The board 202 may be placed with a desired orientation with a front face up or down and a back face pointed in the opposite direction. The edges of the board 202 may then be oriented horizontally to the sides and the ends may be oriented to pass through the saw system 10 linearly along wood path 198. For purposes of this example, the board 202 may be best illustrated as a standard 1"×6" (¾"×5½" actual) with a 16' length. Thus, according to this example the one-inch edges may be oriented to the side while the six-inch faces may point to the top and bottom.

Prior to inserting the board 202 into the saw system 10, an operator may utilize the control panel 18 to pre-select settings relating to the board 202 size, the specific defects to be identified, the specific defects to be removed, the desired board lengths (e.g. a cut list), and the level of quality (such as the National Hardwood Lumber Association (NHLA) grade) desired for each face of the wood 200. Once these and other inputs are entered, the coarse adjustment mechanism 80 may collectively move the guide rollers 36 in each unit lower or higher to accommodate the expected board thickness.

Next, the board 202 may be moved by the feeder apparatus laterally into and through the entrance 68 on the first side 62 of the scanning unit 12. As the feeder moves the board 202 into the scanning unit 12, the forward end thereof will contact both the rollers 31 of the first roller set 32 as well as the first of the plurality of guide rollers 36. Then, as the front edge (leading edge) passes each of the guide rollers 36, each roller will be moved, via pneumatic actuators 40, to drop down and contact the top face of the board 202 to help guide it along the wood path 198 while the first roller set 32 will continue pull the board 202 into the scanning unit 12. As the board 202 moves into the scanning unit 12, the lower and upper optical scanners 24A, 24B will scan the upper and lower faces of the board 202 while the scanning lasers 26 will project onto the board 202 to detect surface defects and depth variations thereof. The optical scanners 24A, 24B are optimized to view a small portion of the board 202 at a time to create a stitched together image of the board 202 as it moves through the scanning unit 12. After being scanned, the leading edge of the board 202 will next encounter the second roller set 34 which will continue to move the board 202 through the scanning unit 12 and into the transition unit 14 via the exit 70 of the scanning unit 12 and entrance 120 of the transition unit 14. The optical scanners 24A, 24B and scanning lasers 26 will continue to scan each section of the board 202 as it moves through the scanning unit 12 and into the transition unit 14.

As the leading edge enters the transition unit 14, it will engage the third roller set 94 which may continue to pull the board 202 into the transition unit 14. Next, the leading edge will engage the fourth roller set 96, which will further assist in moving the board 202 through the transition unit 14. As with scanning unit 12, the guide rollers 36 will be moved via pneumatic actuators 40 to drop down and contact the top face of the board 202 to help guide it through the wood path.

Third and fourth roller sets 94, 96 will continue to move the board 202 through the transition unit 14 and into the cutting unit 16 via the exit 122 of the transition unit 14 and entrance 172 of the cutting unit 16. Once the leading edge moves into the cutting unit 16, it will encounter the rollers 31 of the fifth and sixth roller sets 140, 142 which will move the board 202 into position over the blade slot 162 and saw blade 146.

As the board 202 moves through the scanning unit 12, the transition unit 14, and into the cutting unit 16, the lower and upper optical cameras 24A, 24B and the scanning lasers 26 will continue to scan the later portions of the board 202. These scan results will be communicated in real time to the cutting unit 16 via the one or more computers within the saw system 10, such as through computers in the scanning unit 12 and cutting unit 16, for example.

The board 202 will continue to move through the cutting unit 16 and the leading edge thereof will encounter the seventh roller set 144 after it passes over the saw blade 146 slot 162. The board 202 will continue to move along wood path until a cut point, as determined by either the optical scanners 24 (such as to remove a defect) or as determined by a preset board length (such as determined by the desired end product length and detected by one or more of the scanners 24A, 24B, lasers 26, or sensors 194), is positioned over the saw blade 146 and blade slot 162. At this point, the first through seventh servo motors 28, 30, 90, 92, 134, 136, and 138 will momentarily stop, thus stopping the roller sets 32, 34, 94, 96, 140, 142, and 144, thereby stopping the board 202. Simultaneously, or in rapid succession, the blade extension mechanism 150 will activate and will drive the saw blade 146 upwards out of the blade slot 162 and through the board 202. As soon as the board 202 is cut, seventh servo motor 138 and seventh roller set 144 may activate slightly before first through sixth servo motors 28, 30, 90, 92, 134, and 136 and roller sets 32, 34, 94, 96, 140, and 142 activate to rapidly carry away the cut piece of the board 202. This may prevent the cut piece of the board 202 from impeding the rest of the board's 202 progress through the saw system 10. Alternatively, all seven servo motors 28, 30, 90, 92, 134, 136, and 138 may activate simultaneously, but with the seventh servo motor 138 activating at a higher speed which may result in the seventh roller set 144 rotating at a faster RPM to again move the cut piece away faster than the remaining board 202 is able to be moved into position for the next cut.

As the board 202 moves through the saw system 10 down wood path 198, the optical scanners 24 and scanning lasers 26 of scanning unit 12 will continue to scan and communicate in real time with the cutting unit 16 to optimize the cuts and to remove defects from the board 202. With the example above, a 16' board may have the leading end being cut by cutting unit 16 while the trailing end is still being scanned. Shorter boards may complete their scans prior to, or during the cutting process, thus freeing the scanning unit 12 to begin scanning the next board in line. According to one aspect, the focal point of the optical scanners 24 may be spaced apart from the saw blade 146 by a distance of approximately 140 inches (approximately 11'8"). Therefore, any boards longer than 140 inches in length may simultaneously be scanned and cut, as discussed above. According to another aspect, this distance may vary depending on the desired implementation of system 10. Further according to this aspect, saw system 10 may be arranged or configured to allow for simultaneous scanning and cutting of boards of any size by increasing or decreasing the length of path 198. For example, when scanning and cutting boards shorter than 11'8", path 198 may be reduced by reducing the size of or eliminating transition unit 14, or by reducing the number of and/or distance between rollers 31 within any or all units. When cutting boards longer than 11'8", length of path 198 may be increased by enlarging the transition unit 14, adding a second transition unit 14, or by increasing the number of and/or distance between rollers 31 in any or all units of saw system 10. This adjustability and flexibility in system 10 may allow for simultaneous scanning and cutting of nearly any length board while still eliminating the post scanning queue of current systems and while significantly reducing the required floor space for such systems.

According to another aspect, the speed of system 10 and its components, such as rollers 31, servo motors 28, 30, 90, 92, 134, 136, and 138, and or saw blade 146 and its components, may be increased or decreased to likewise increase or decrease the time interval between scanning and cutting. For example, when shorter boards are being cut, saw system 10 may increase its processing speed to move a board faster between the scanning unit 12 and the cutting unit 16. Where a longer board is being cut, saw system 10 may reduce processing speed to move a board more slowly between scanning unit 12 and cutting unit 14. Further according to this aspect, the time between scanning a first portion of a board and cutting that same portion may be less than three (3) seconds, with an approximately twelve (12) foot long board being completely scanned and cut in less than ten (10) seconds. According to another aspect, these times may range between one and ten (1-10) seconds between the first scan and the first cut of one board, and between ten and thirty (10-30) seconds to fully scan and cut a twelve (12) foot board. Thus, when continuously feeding boards into saw system 10, processing times for a twelve (12) foot board may be ten (10) seconds or less per board, with less than three (3) seconds elapsing between the final cut of a first board and the first cut of a second board. According to this example then, an entire first board may be processed and a first cut made on second board may occur in under thirteen (13) seconds total.

As a general rule, each time the leading edge passes under a guide roller 36 (and/or past a specific sensor 194), the saw system 10 will activate the pneumatic actuators 40 to rotate each guide roller 36 downward to contact the top face of the board 202. These guide rollers 36 may provide a light pressure to the top face of the board 202 to keep the bottom face in constant contact with each roller set to allow efficient movement through the saw system 10. Each guide roller is not rotated down and into contact with the front face of the board 202 until the leading edge passes a certain point below each roller to avoid damage and/or breakage of the guide rollers 36. By allowing a "cushion" of space, the guide rollers 36 do not take repeated impacts from the leading edge of boards moving through the saw system 10, thus prolonging their usable life. In the instance where a board that is too thick is inadvertently sent through saw system 10, the dual arrangement of pneumatic actuators 40 may permit the guide rollers 36 to be driven upwards to absorb the impact from the leading edge of that inadvertently fed board. As such an instance is rare, the occasional impact is not likely to cause significant damage due to the ability of the guide rollers 36 to deflect upwards and out of the way of the board 202.

Additionally, as the board 202 moves along wood path 198, it will encounter the first through seventh roller sets 32, 34, 94, 96, 140, 142, and 144 in order. The first through seventh servo motors 28, 30, 90, 92, 134, 136, and 138 may be activated ahead of the leading edge of the board 202 to match the speed of the roller set 32, 34, 94, 96, 140, 142, or 144 immediately upstream thereof. This early activation allows the rollers 31 in each roller set 32, 34, 94, 96, 140, 142, and 144 to reach operational speed to keep the board 202 moving through the wood path without damage or slowing. Similarly, servo motors 28, 30, 90, 92, 134, 136, and 138 and roller sets 32, 34, 94, 96, 140, 142, and 144 may be activated or deactivated as needed depending upon the presence of a board within the saw system 10. For example, servo motors 28, 30, 90, 92, 134, 136, and 138 and roller sets 32, 34, 94, 96, 140, 142, and 144 may be activated according to the process described above, and deactivated when the trailing edge of a board passes by the last roller 31 of each set 32, 34, 94, 96, 140, 142, and 144. Further, servo motors and roller sets 32, 34, 94, 96, 140, 142, and 144 may be activated at any speed relative to the speed of the servo motor 28, 30, 90, 92, 134, 136, or 138 and roller set 32, 34, 94, 96, 140, 142, or 144 immediately upstream or downstream thereof and may be re-synched with other servo motors 28, 30, 90, 92, 134, 136, and 138 and roller sets 32, 34, 94, 96, 140, 142, and 144 as necessary. By way of the non-limiting example presented above, the seventh servo motor 138 and seventh roller set 144 may activate sooner and/or at a higher speed than the sixth servo motor 136 and sixth roller set 142 immediately after a cut is made to move the cut piece of wood 200 away rapidly. As soon as the trailing edge of the cut piece passes by the last roller 31 of seventh roller set 144, the seventh servo motor 138 and seventh roller set 144 may be slowed to sync its speed with the sixth servo motor 142 and sixth roller set 142 to prevent damage to the board 202 as it moves into position for the next cut.

The physical isolation of the scanning unit 12 from the cutting unit 16 may reduce or eliminate vibration in the scanning unit 12 through employment of multiple housings or other suitable vibration reduction or elimination methods. Similarly, the inclusion of the transition unit 14 between the scanning unit 12 and the cutting unit 16 further isolates the optical scanners 24 from the cutting unit 16 to further provide a buffer to minimize or eliminate vibration transfer therebetween. The housings of any or all of the scanning unit 12, transition unit 14, and/or cutting unit 16 may further include vibration dampening materials to further reduce vibrations transmitted therebetween. The prevention of vibration in the scanning unit 12 is valuable as the lower and upper optical scanners 24A, 24B are then able to maintain their precise accuracy as the board 202 passes through scanning unit 12 to insure proper cut positions on the board 202 by the cutting unit 16.

The speed of the saw blade 146, or more particularly the speed at which the saw blade 146 is raised and lowered by the blade extension mechanism 150, may vary to allow for cutting a wider board. For example, a board with a width of four inches may not require any reduced speed as the saw blade 146 may sufficiently cut the entire width of the board 202 in a single pass at full speed whereas a 16-inch wide board may take longer as the saw blade 146 is required to travel further to cut the full width of the board 202. Wider boards have more surface area against the saw blade 146 which may increase the chance of binding the blade 146 or splintering the wood, so a slower cut speed is desirable to prevent such issues. Accordingly, the upstroke speed of the saw blade 146 as it rises out of the blade slot 162 in the cutting unit 16 may be reduced to allow the blade 146 to fully cut through the wider board. The lowering of the saw blade 146 may then be accelerated back to full speed to reduce the delay between cuts introduced by slowing the upstroke. Depending on the width and thickness of the board 202, the entire saw system 10 may be slowed to insure proper cuts with minimal scarring, splintering, or other damage to the wood product. As the saw system 10 may be equipped to detect the width and the thickness of the board 202 as it passes into and through the scanning unit 12, the control software for the saw system 10 may automatically adjust the speed of the rollers 31 and/or the saw blade 146 itself to accommodate boards of varying thicknesses and widths. According to another aspect, the system may be preset for boards of a specific width and/or thickness to allow for rapid and continuous operation of the automated saw system 10.

As compared to current systems, the present saw system 10 may generate uniform and consistent results in producing lengths of board while reducing the overall footprint of the apparatus and eliminating the need for a second feeder and a queue between the scanning unit 12 and cutting unit 16 thereof. Further, as the scanning unit 12 is able to scan and communicate to the cutting unit 16 in real time, the board 202 being scanned may be simultaneously cut, or alternatively the board 202 being scanned may be the next board to be cut, further illustrating the elimination of the secondary queue and feeder systems of present saw systems 10.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of technology disclosed herein may be implemented using hardware, software, or a combination thereof. When implemented in software, the software code or instructions can be executed on any suitable processor or collection of processors, whether provided in a single computer or distributed among multiple computers. Furthermore, the instructions or software code can be stored in at least one non-transitory computer readable storage medium.

Also, a computer or smartphone utilized to execute the software code or instructions via its processors may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers or smartphones may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software/instructions that are executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, USB flash drives, SD cards, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above.

The terms "program" or "software" or "instructions" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

All definitions, as defined and used herein, should be understood to control over dictionary definitions, definitions in documents incorporated by reference, and/or ordinary meanings of the defined terms.

"Logic", as used herein, includes but is not limited to hardware, firmware, software, and/or combinations of each to perform a function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, an electric device having a memory, or the like. Logic may include one or more gates, combinations of gates, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Furthermore, the logic(s) presented herein for accomplishing various methods of this system may be directed towards improvements in existing computer-centric or internet-centric technology that may not have previous analog versions. The logic(s) may provide specific functionality directly related to structure that addresses and resolves some problems identified herein. The logic(s) may also provide significantly more advantages to solve these problems by providing an exemplary inventive concept as specific logic structure and concordant functionality of the method and system. Furthermore, the logic(s) may also provide specific computer implemented rules that improve on existing technological processes. The logic(s) provided herein extends beyond merely gathering data, analyzing the information, and displaying the results. Further, units or all of the present disclosure may rely on underlying equations that are derived from the specific arrangement of the equipment or components as recited herein. Thus, units of the present disclosure as it relates to the specific arrangement of the components are not directed to abstract ideas. Furthermore, the present disclosure and the appended claims present teachings that involve more than performance of well-understood, routine, and conventional activities previously known to the industry. In some of the method or process of the present disclosure, which may incorporate some aspects of natural phenomenon, the process or method steps are additional features that are new and useful.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have units that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, any method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. A method of cutting a piece of wood comprising:
   inserting a first end of a piece of wood into a scanning unit of an automated saw system;
   scanning the first end of the piece of wood for one or more defects via at least one optical scanner;
   directing the piece of wood along a path through the saw system directly into a cutting unit via at least one roller set operable to move the piece of wood through the scanning unit and into the cutting unit; and
   cutting the first end of the piece of wood while simultaneously scanning a second end of the piece of wood with the at least one optical scanner.

2. The method of claim 1 wherein the at least one optical scanner further comprises:
   a first optical scanner below the path; and
   a second optical scanner above the path.

3. The method of claim 2 wherein scanning the first and second sends of the piece of wood is accomplished by the first optical scanner and the second optical scanners.

4. The method of claim 3 wherein the scanning unit communicates cut positions on the piece of wood to the cutting unit in real time.

5. The method of claim 1 further comprising:
   moving the piece of wood through the scanning unit and into the cutting unit via at least one roller set in the scanning unit and at least another roller set in the cutting unit.

6. The method of claim 5 further comprising:
   moving the piece of wood through a transition unit after the scanning unit and before the cutting unit.

7. The method of claim 5 further comprising:
   stopping the piece of wood to place the first end of the piece of wood directly over a saw blade within the cutting unit.

8. The method of claim 7 wherein stopping the piece of wood over the saw blade is accomplished by stopping the at least one roller set in the scanning unit and the at least one roller set in the cutting unit.

9. The method of claim 8 further comprising:
   engaging the at least one roller set in the cutting unit before engaging the at least one roller set in the scanning unit after cutting the first end of the piece of wood to remove the cut first end of the piece of wood from the cutting unit.

10. The method of claim 1 wherein the path through the saw system is linear from the scanning unit through the cutting unit.

11. The method of claim 1 wherein cutting the piece of wood further comprises:
    cutting the piece of wood to remove a defect therefrom.

12. The method of claim 1 wherein cutting the piece of wood further comprises:
    cutting the piece of wood to a pre-specified length.

13. The method of claim 1 wherein cutting the piece of wood further comprises:
    cutting the piece of wood to a pre-specified length and to remove a defect therefrom.

14. The method of claim 1 wherein the distance between a focal point of the at least one optical scanner and a saw blade in the cutting unit is less than twelve feet.

15. The method of claim 1 wherein the time elapsed between scanning the first end of the piece of wood and cutting the first end of the piece of wood is less than three seconds.

16. A method of optimized wood production comprising:
    inserting a first piece of wood into a scanning unit of an automated saw system;
    scanning a first end of the first piece of wood for one or more defects via at least one optical scanner;
    directing the first end of the first piece of wood along a path through the saw system directly into a cutting unit via at least one roller set operable to move the piece of wood through the scanning unit and into the cutting unit;
    cutting the first end of the first piece of wood with the cutting unit while simultaneously scanning a second end of the first piece of wood with the at least one optical scanner;
    directing the second end of the first piece of wood to the cutting unit while simultaneously inserting a second piece of wood into the scanning unit; and
    cutting the second end of the first piece of wood with the cutting unit while simultaneously scanning a first end of the second piece of wood with the at least one optical scanner.

17. The method of claim 16 wherein the distance between a focal point of the at least one optical scanner and a saw blade in the cutting unit is less than twelve feet.

18. The method of claim 16 wherein the time elapsed between scanning the first end of the first piece of wood and cutting the first end of the first piece of wood is less than three seconds.

19. The method of claim 16 wherein the time elapsed between scanning the first end of the first piece of wood and cutting the first end of the second piece of wood is less than thirteen seconds.

20. The method of claim 16 further comprising:
removing the first piece of wood from the cutting unit while simultaneously directing the first end of the second piece of wood into the cutting unit.

21. The method of claim 20 further comprising:
cutting the first end of the second piece of wood with the cutting unit while simultaneously scanning a second end of the second piece of wood with the at least one optical scanner.

22. The method of claim 21 further comprising:
directing the second end of the second piece of wood to the cutting unit while simultaneously inserting a third piece of wood into the scanning unit; and
cutting the second end of the second piece of wood with the cutting unit while simultaneously scanning a first end of the third piece of wood with the at least one optical scanner.

23. The method of claim 22 further comprising:
continuously inserting subsequent pieces of wood into the scanning unit while cutting a first end of each subsequent piece of wood while scanning a second portion thereof.

24. The method of claim 22 further comprising:
continuously inserting subsequent pieces of wood into the scanning unit; and
cutting a second end of each subsequent piece of wood while scanning a first end of the next piece of wood inserted into the scanning unit.

\* \* \* \* \*